(12) United States Patent
Xie et al.

(10) Patent No.: US 12,221,424 B2
(45) Date of Patent: Feb. 11, 2025

(54) 3-TETRAZOLYLMETHYL-1,3,5-TRIAZIN-2,4-DIONE COMPOUND INHIBITING CORONAVIRUS 3CL PROTEASE ACTIVITY AND PREPARATION METHOD AND USE THEREOF

(71) Applicants: SHAANXI PANLONG PHARMACEUTICAL CO., LTD., Shaanxi (CN); XIXIAN NEW DISTRICT FENGHOU ORIGINAL PHARMACEUTICAL TECHNOLOGY CO., LTD., Shaanxi (CN)

(72) Inventors: Xiaolin Xie, Xi'an (CN); Dezhu Zhang, Xi'an (CN); Zhao Ma, Xi'an (CN); Boyang Li, Xi'an (CN); Xuhua Zhou, Xi'an (CN); Chengyuan Liang, Xi'an (CN); Liang Xin, Xi'an (CN); Lei Tian, Xi'an (CN); Jingyi Li, Xi'an (CN); Kangxiong Wu, Xi'an (CN); Shaojun Zhang, Xi'an (CN); Xiuding Yang, Xi'an (CN); Sundian Liu, Xi'an (CN); Yuting Liu, Xi'an (CN)

(73) Assignees: SHAANXI PANLONG PHARMACEUTICAL CO., LTD., Shaanxi (CN); XIXIAN NEW DISTRICT FENGHOU ORIGINAL PHARMACEUTICAL TECHNOLOGY CO., LTD., Shaanxi (CN)

( * ) Notice: Subject to any disclaimer, the term of this patent is extended or adjusted under 35 U.S.C. 154(b) by 122 days.

(21) Appl. No.: 18/186,158

(22) Filed: Mar. 18, 2023

(65) Prior Publication Data
US 2023/0391736 A1 Dec. 7, 2023

(51) Int. Cl.
*A61P 31/14* (2006.01)
*C07D 257/04* (2006.01)
*C07D 403/14* (2006.01)

(52) U.S. Cl.
CPC ............ *C07D 257/04* (2013.01); *A61P 31/14* (2018.01)

(58) Field of Classification Search
CPC ...... A61P 31/14; C07D 257/04; C07D 403/14
See application file for complete search history.

(56) References Cited

U.S. PATENT DOCUMENTS 11,612,603 B1 * 3/2023 Liang ...................... A61P 31/14
514/241

* cited by examiner

*Primary Examiner* — Danah Al-Awadi
*Assistant Examiner* — Alison Azar Salamatian

(57) ABSTRACT

The present invention relates to the technical field of medicinal chemistry, and particularly to a method for preparing a 3-tetrazolylmethyl-1,3,5-triazin-2,4-dione compound inhibiting coronavirus 3CL protease activity and use thereof. Specifically, a compound of Formula I, or a pharmaceutically acceptable salt, or an optical isomer, or an isotope-substituted form thereof is provided. The compound effectively inhibits the SARS-CoV-2 $3CL^{pro}$ activity, and is useful in the preparation of a SARS-CoV-2 $3CL^{pro}$ inhibitor to block the replication and transcription of SARS-CoV-2 viruses in patients. The compound prepared in the present invention has high in-vitro safety, and very good prospect of application in the preparation of SARS-CoV-2 $3CL^{pro}$ inhibitors and anti-SARS-CoV-2 drugs.

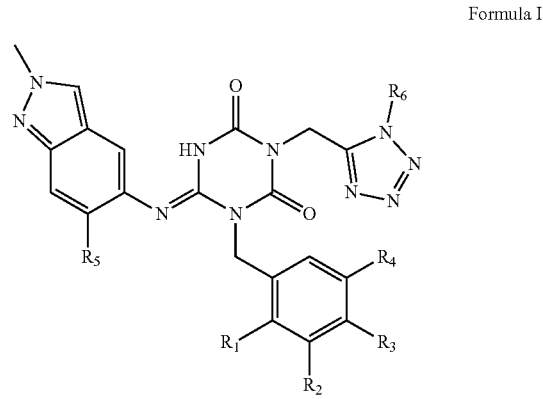

Formula I

4 Claims, 8 Drawing Sheets

3-TETRAZOLYLMETHYL-1,3,5-TRIAZIN-2,4-DIONE COMPOUND INHIBITING CORONAVIRUS 3CL PROTEASE ACTIVITY AND PREPARATION METHOD AND USE THEREOF

This application claims priority to Chinese Patent Application No. 202210916662.8, filed on Jun. 1, 2022, which is incorporated by reference for all purposes as if fully set forth herein.

TECHNICAL FIELD

The present invention relates to the technical field of medicinal chemistry, and particularly to a 3-tetrazolylmethyl-1,3,5-triazin-2,4-dione compound inhibiting coronavirus 3CL protease activity, and a preparation method and use thereof.

BACKGROUND

The persistent Corona Virus Disease 2019 (2019-NCoVID) pandemic causes an alarming situation, results in large cases of deaths and serious economic loss, and poses a huge threat to global health and safety. So far, the variant strains having stronger spreading power, such as Delta and Omichoron, are constantly emerging. However, no drugs specific for SARS-CoV-2 are developed currently, so there is a need for a drug that can effectively suppress the new coronavirus.

3CL protease is an enzyme in coronavirus. In fact, 3CL$^{pro}$ has been shown to be a target for the development of drug against SARS, MERS, and SARS-Cov-2 coronavirus. 3CL$^{pro}$ (3C-like protease, also known as the main protease M$^{pro}$), as an important non-structural protein in coronavirus, has a cleavage site specificity similar to that of 3CL protease of microRNA viruses, and plays a quite critical role in the replication and transcription of progeny viruses. 3CL$^{pro}$ is a cysteine protease of about 33 kDa consisting of 306 amino acids (much smaller than S protein), which can specifically recognize and cleave 11 cleavage sites of non-structural proteins NSP4-NSP16, to release other non-structural proteins in coronavirus. The non-structural proteins NSP4-NSP16 released by autohydrolysis and cleavage by 3CL$^{pro}$ are the sites of viral genome replication and transcription, and are involved in the post-translational protein cleavage, modification, nucleic acid synthesis and other important life processes. Inhibition of 3CL$^{pro}$ can effectively block the process of RNA replication and transcription, thus blocking the proliferation of viruses. This highlights the importance of 3CL proteases in the design of effective drugs against COVID-19.

SUMMARY OF THE INVENTION

To overcome the shortcomings existing in the prior art, an object of the present invention is to provide a 3-tetrazolylmethyl-1,3,5-triazin-2,4-dione compound inhibiting coronavirus 3CL protease activity and a preparation method and use thereof. The compound is useful in the treatment of coronavirus-induced diseases.

To achieve the above object, the following technical solutions are adopted in the present invention.

Compared with the prior art, the present invention has the following beneficial effects:

A 3-tetrazolylmethyl-1,3,5-triazin-2,4-dione compound inhibiting coronavirus 3CL protease activity is provided in the present invention. The activity test results in inhibiting 3CL$^{pro}$ show that the compound synthesized in the present invention has a potent inhibition on 3CL$^{pro}$, and the preferred Compounds 1, 12, 15, 16 and 17 have an IC$_{50}$ value for 3CL$^{pro}$ that is below 200 nM. Compared with the drugs S-216722 and PF-07321332 against new coronaviruses, Compound 1 has the most desirable inhibitory activity. The cytotoxicity test results show that the inhibition rates of Compound 1 on HepG2 cells and HEK293 cells are lower than those of PF-07321332 and S-217622 at any concentrations, and the toxicity on A549 cells is better than that of PF-07321332 and S-217622 at low concentrations, so it can be developed and applied as anti-coronavirus drugs.

A method for synthesizing the 3-tetrazolylmethyl-1,3,5-triazin-2,4-dione compound inhibiting coronavirus 3CL protease activity is provided in the present application. The synthesis method has simple operations and low requirements for reaction apparatus, the raw materials used are readily available, and less pollution is caused, so the method is suitable for use in industrial production.

DETAILED DESCRIPTION

Figure 1:
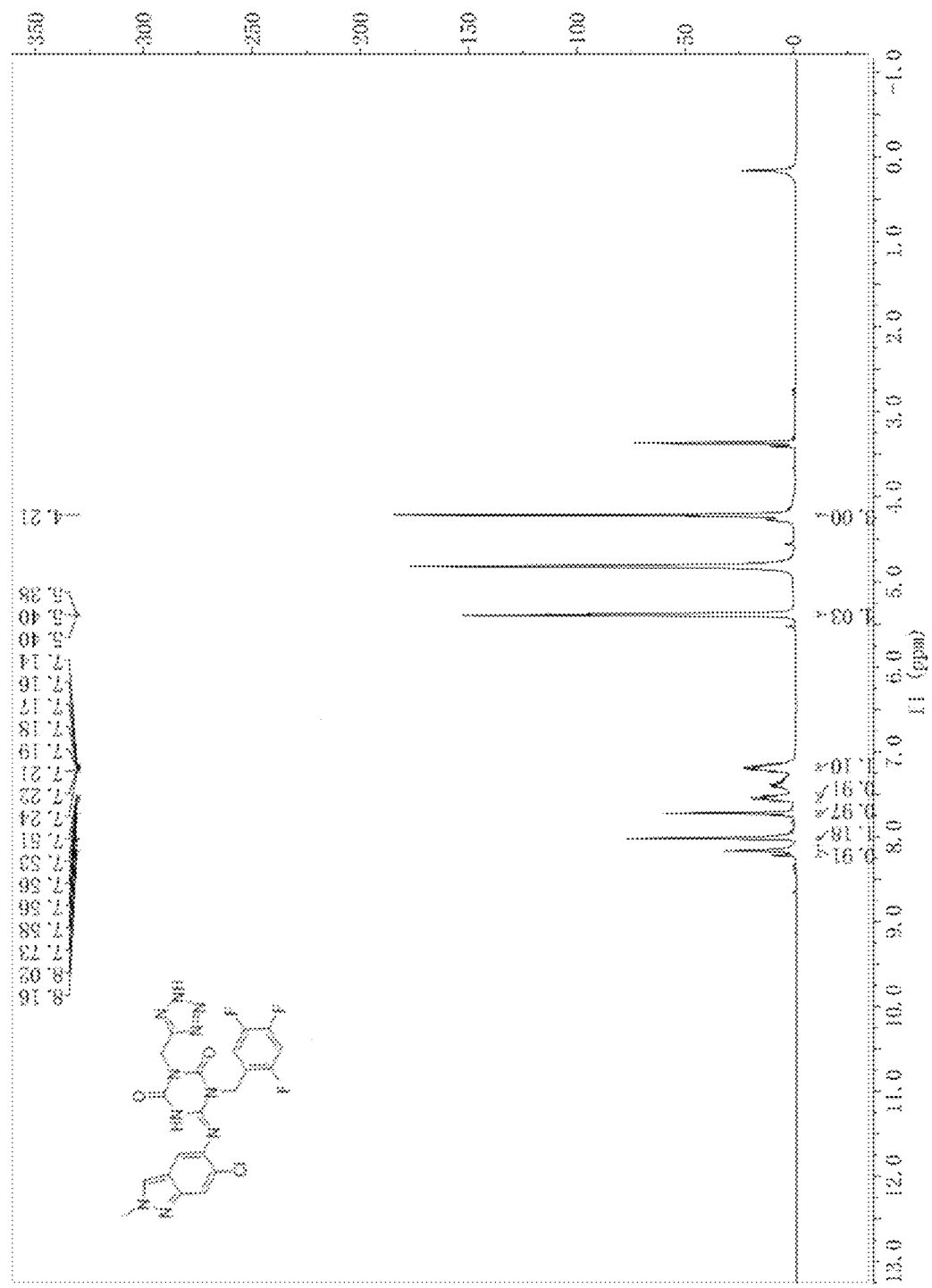
FIG. 1 is a $^1$H NMR spectrum of Compound 1 of the present invention in deuterated MeOD.

For better understanding of the technical solutions of the present invention by those skilled in the art, the technical solutions in the embodiments of the present invention will be described clearly and fully with reference to the accompanying drawings in the embodiments of the present invention. Apparently, the embodiments described are merely some, rather than all of the embodiments of the present invention. All other embodiments obtained by a person of ordinary skill in the art without creative efforts based on the embodiments of the present invention shall fall within the protection scope of the present invention.

It is to be understood that in the specification, claims, and accompanying drawings of the present invention, the terms such as "first" and "second" are intended to distinguish similar objects rather than indicate a particular order or precedence. It should be understood that the data thus used are interchangeable where appropriate so that embodiments of the present invention described herein can be implemented in an order other than those illustrated or described herein. In addition, the term "include", "have" and any variants thereof are intended to cover non-exclusive embracing. For example, a process, method, system, product, or device including a series of steps or units is not limited to the clearly listed steps or units; and instead, further includes a step or unit that is not specifically listed, or that is intrinsic to the process, method, product, or device.

The present invention will be further described in detail below with reference to accompanying drawings.

The present invention provides a 3-tetrazolylmethyl-1,3,5-triazin-2,4-dione compound inhibiting coronavirus 3CL protease activity, which is a compound of Formula I or a pharmaceutically acceptable salt thereof, and a solvate, an enantiomer, a diastereomer, or a tautomer of the compound of Formula I or the pharmaceutically acceptable salt thereof, or a mixture thereof at any ratio, including a racemic mixture.

The compound of Formula I has a structural formula shown below:

I

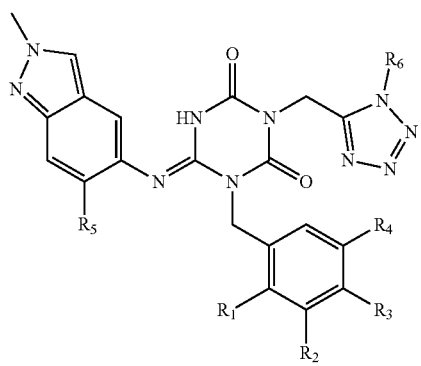

in which $R_1$, $R_2$, $R_3$ and $R_4$ are each independently selected from hydrogen, methyl, t-butyl, methoxy, difluoromethyl, trifluoromethyl, trifluoromethoxy, nitro, halo, phenyl and heteroarylcyclyl;

$R_5$ is hydrogen or halo; and $R_6$ is hydrogen or an alkyl or cycloalkyl having 1 to 4 carbon atoms.

The term "halo" represents fluoro, chloro, bromo, or iodo.

The term pharmaceutically acceptable salt is a salt of the 3-tetrazolylmethyl-1,3,5-triazin-2,4-dione compound inhibiting coronavirus 3CL protease activity with hydrochloric acid, hydrobromic acid, sulfuric acid, nitric acid, phosphoric acid, acetic acid, fumaric acid, maleic acid, oxalic acid, malonic acid, succinic acid, citric acid, malic acid, methansulfonic acid, ethansulfonic acid, benzenesulfonic acid, toluenesulfonic acid, glutamic acid or aspartic acid.

A method for preparing a 3-tetrazolylmethyl-1,3,5-triazin-2,4-dione compound inhibiting coronavirus 3CL protease activity provided in the present invention is as follows.

(1) 3-t-butyl-6-(ethylthio)-1,3,5-triazin-2,4(1H,3H)-dione as a raw material is alkylated with a benzyl bromide compound, to obtain Compounds a1-a24.

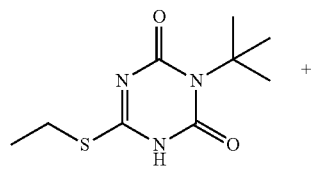

+

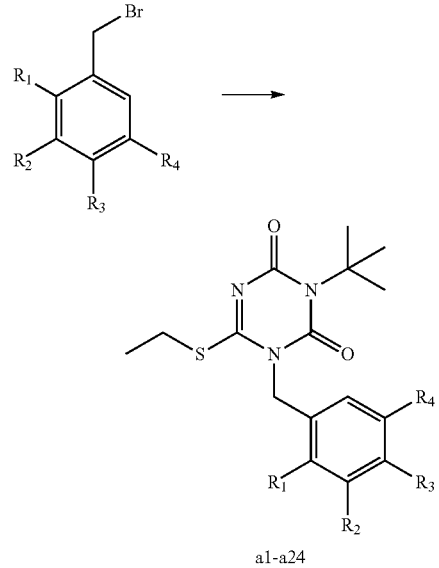

a1-a24

The molar ratio of 3-t-butyl-6-(ethylthio)-1,3,5-triazin-2,4(1H,3H)-dione to the benzyl bromide compound is 1:1.1; and the solvent used during the synthesis of Compounds a1-a24 is acetonitrile. The reaction is carried out in the presence of potassium carbonate under reflux by heating. The benzyl bromide compound is:

| $R_1$ = | $R_2$ = | $R_3$ = | $R_4$ = | Structure |
|---|---|---|---|---|
| —F | —H | —F | —F | Br-CH2-C6H2F3 |
| —H | —H | —H | —H | Br-CH2-C6H5 |
| —H | —H | —CH3 | —H | Br-CH2-C6H4-CH3 |
| —H | —H | —C(CH3)3 | —H | Br-CH2-C6H4-C(CH3)3 |
| —H | —H | —NO2 | —H | Br-CH2-C6H4-NO2 |

| $R_1=$ | $R_2=$ | $R_3=$ | $R_4=$ | Structure |
|---|---|---|---|---|
| —H | —H | —OCH$_3$ | —H | 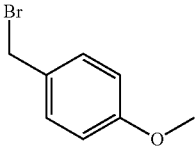 |
| —H | —H | —OCF$_3$ | —H | 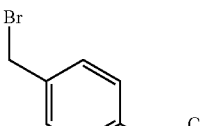 |
| —H | —H | —F | —H | 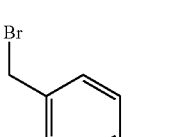 |
| —H | —H | —Cl | —H | 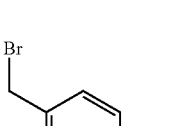 |
| —H | —H | —Br | —H | 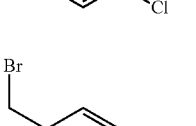 |
| —H | —H | —Ph | —H | 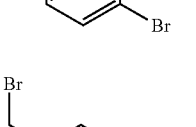 |
| —H | —H | —CF$_3$ | —H | 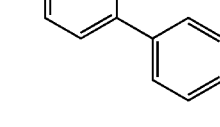 |
| —H | —CH$_3$ | —H | —CH$_3$ | 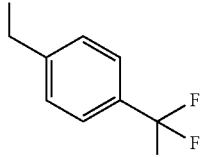 |
| $R_1=$ | $R_2=$ | $R_3=$ | $R_4=$ | Structure |
|---|---|---|---|---|
| —H | —OCH$_3$ | —H | —OCH$_3$ | 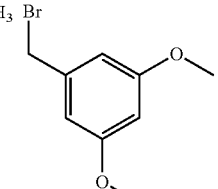 |
| —H | —F | —H | —F | 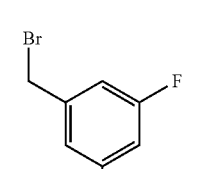 |
(2) The t-butyl group is removed from Compounds a1-a24 prepared in Step (1) to obtain corresponding Compounds b1-b24, which are then respectively reacted with bromoacetonitrile, to obtain corresponding Compounds c1-c24.
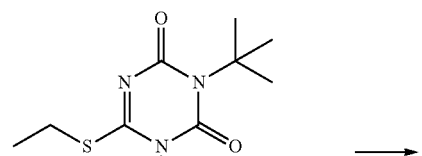
a1-a24
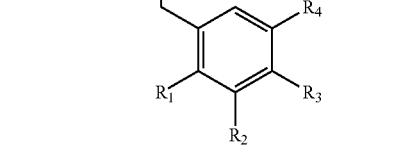
b1-b24

The solvent used in the synthesis of Compounds b1-b24 is trifluoroacetic acid; the molar ratio of Compounds b1-b24 to bromoacetonitrile is 1:1.2; the solvent used in the synthesis of Compounds c1-c24 is acetonitrile, and the reaction is carried out in the presence of potassium carbonate under reflux by heating.

(3) Compounds c1-c24 prepared in Step (2) are respectively reacted with 6-chloro-2-methyl-2H-indazol-5-amine or 2-methyl-5-amino-2H-indazole, to obtain corresponding Compounds d1-d24.

The molar ratio of Compounds c11-c24 to 6-chloro-2-methyl-2H-indazol-5-amine or 2-methyl-5-amino-2H-indazole is 1:1.3; and the catalyst used in the synthesis of Compounds d1-d24 is acetic acid, and the solvent used is t-butanol.

(4) Compounds d1-d15 prepared in Step (3) are respectively reacted with sodium azide, to produce 3-tetrazolylmethyl-1,3,5-triazin-2,4-dione compounds 1-15 of structural Formula I inhibiting coronavirus 3CL protease activity; or Compounds d16-d20 prepared in Step (3) are respectively reacted with sodium azide, to obtain corresponding Compounds e16-e20, which are then further reacted with methyl trifluoromethansulfonate or ethyl trifluoromethansulfonate, to produce 3-tetrazolylmethyl-1,3,5-triazin-2,4-dione compounds 16-20 of structural Formula I inhibiting coronavirus 3CL protease activity; or Compounds d21-d24 obtained in Step (3) are respectively reacted with an azidoalkane compound, to produce 3-tetrazolylmethyl-1,3,5-triazin-2,4-dione compounds 21-24 of structural Formula I inhibiting coronavirus 3CL protease activity.

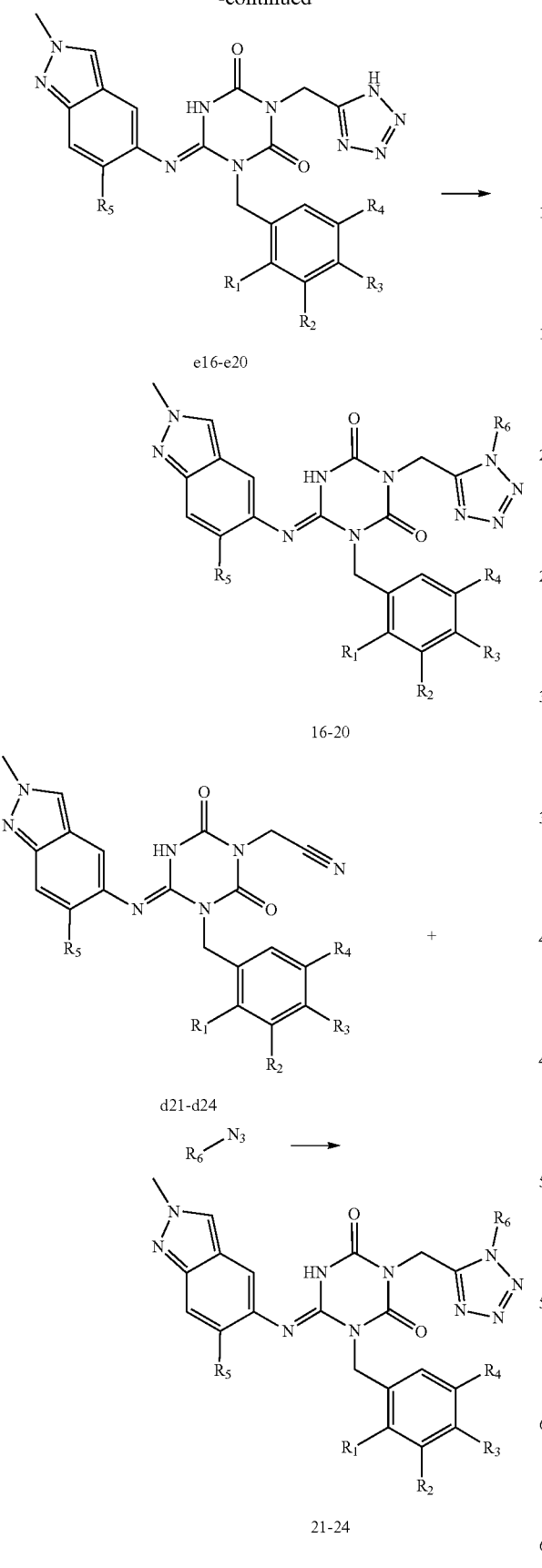

e16-e20

16-20 d21-d24

21-24

The molar ratio of Compounds d1-d20 to sodium azide is 1:1.05, the molar ratio of methyl trifluoromethansulfonate or ethyl trifluoromethansulfonate to Compounds e16-e20 is 1:1.2, and the molar ratio of Compounds d21-d24 to azidoalkane compound is 1:1.2. The solvent used in the synthesis of Compounds 1-15 is N,N-dimethyl amide, and the catalyst used is zinc chloride. The solvent used in the synthesis of Compounds 16-20 is 1,4-dioxane, and the catalyst used is bis(dibenzylideneacetone)palladium, 2-(di-t-butylphosphino)-3,6-dimethoxy-2'-4'-6'tri-1-propyl-1,1'-biphenyl and potassium phosphate. The solvent used in the synthesis of Compounds 21-24 is N,N-dimethyl amide, tetrahydrofuran and water, and the catalyst used is copper sulfate pentahydrate and sodium ascorbate.

1. Specific Synthesis Examples of Compounds 1-24

Representative compounds of the present invention have a structural formula shown below:

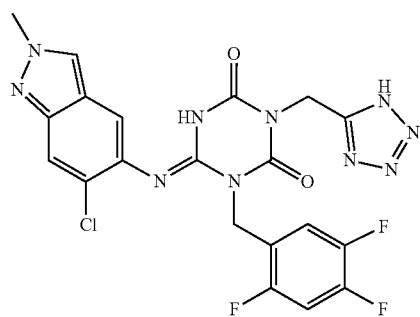

1

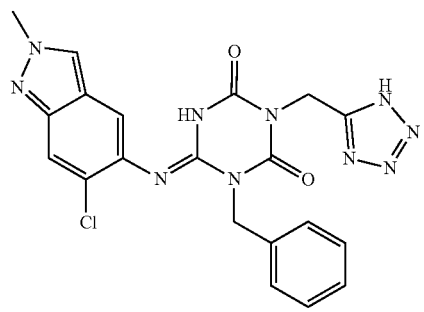

2

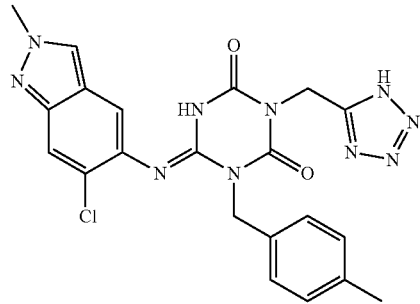

3

4
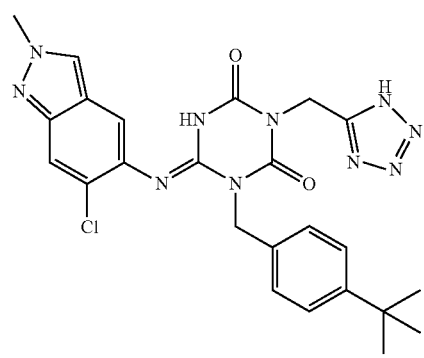
5
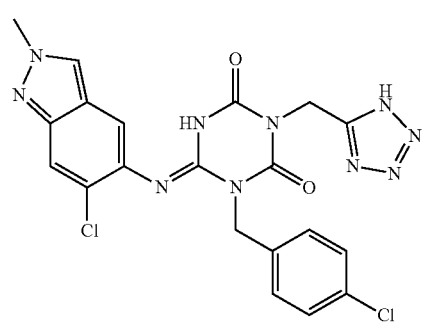
6
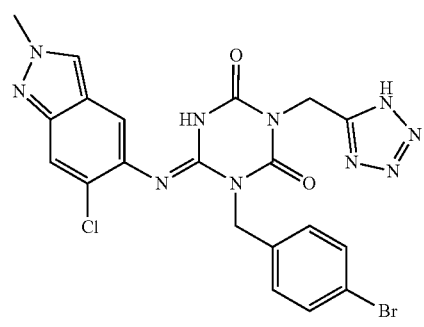
7
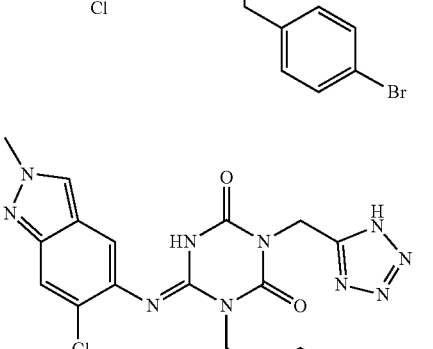
8
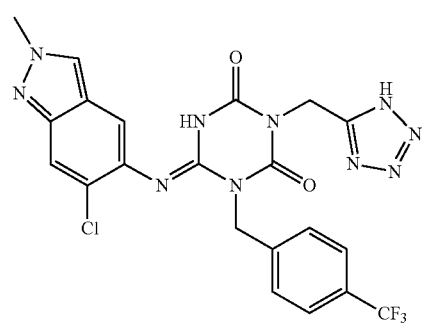
9
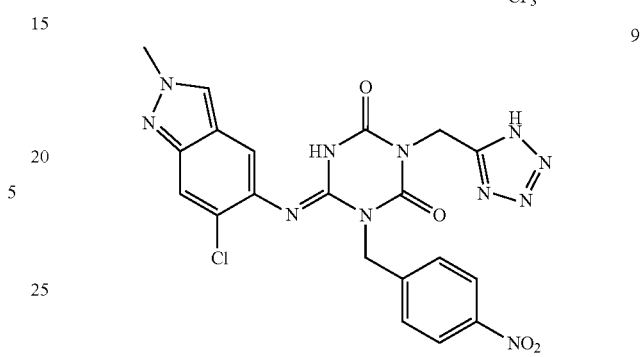
10
11
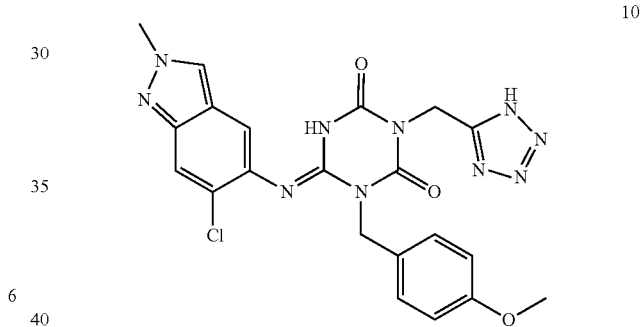
12
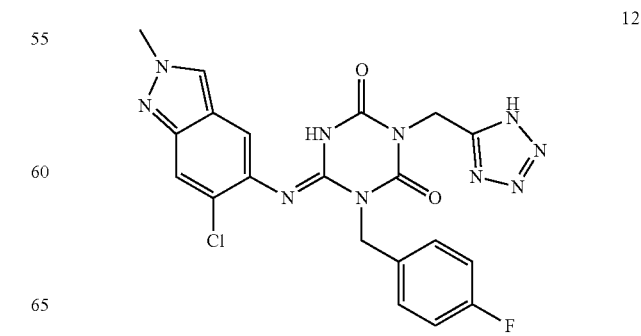

13
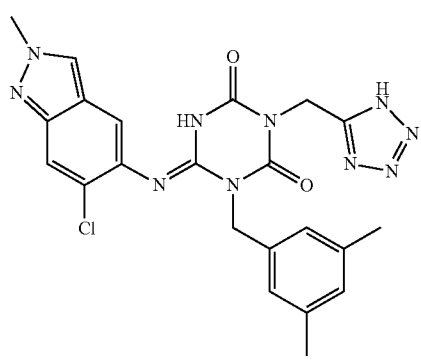
14
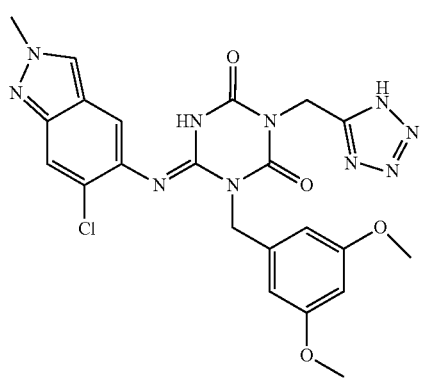
15
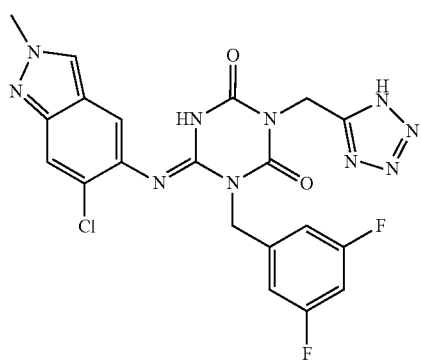
16
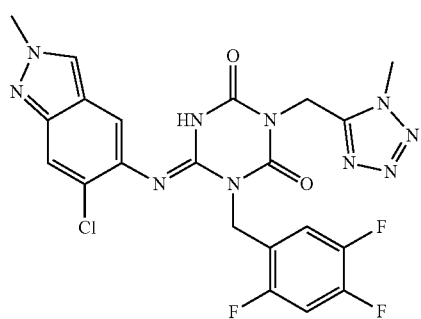
17
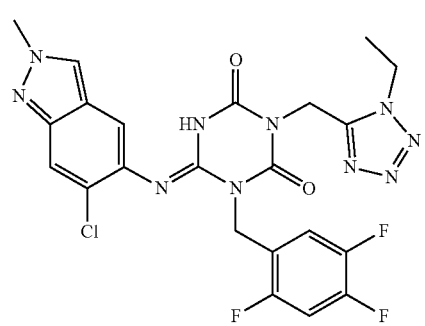
18
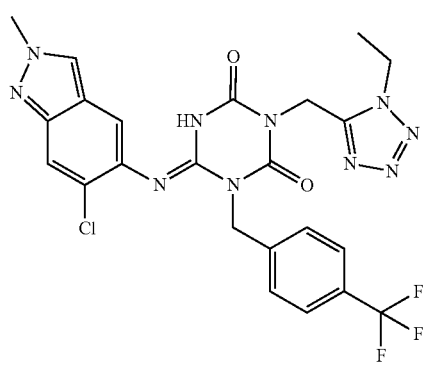
19
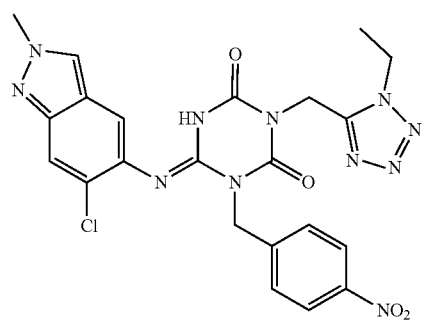
20
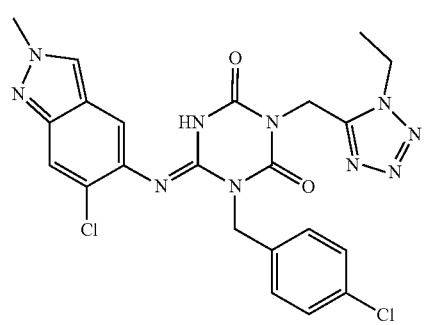
21
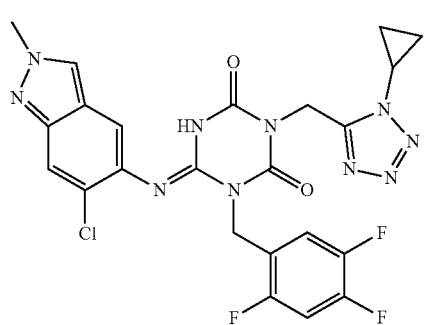

-continued

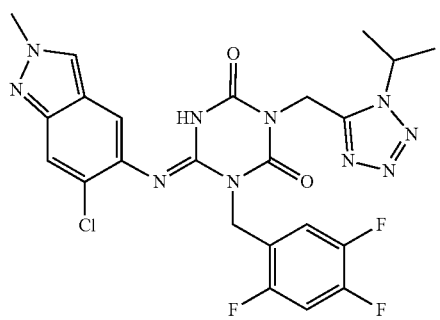

22

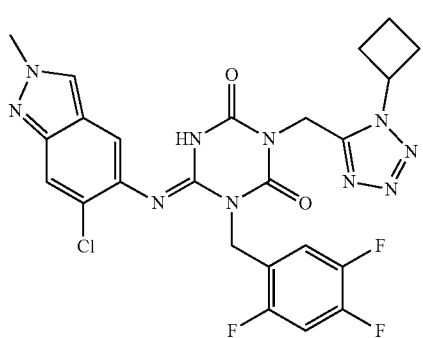

23

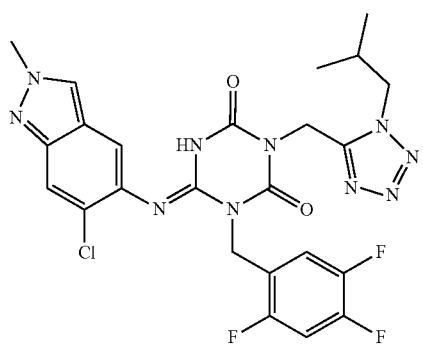

24

Synthesis examples of the compounds are given below.

Example 1

Preparation of Compound 1: (E)-3-(1H-tetrazol-5-yl)methyl-6-(6-chloro-2-methyl-2H-indazol-5-yl)imino)-1-(2,4,5-trifluorobenzyl)-1,3,5-triazin-2,4-dione (1) Preparation of Compound a1

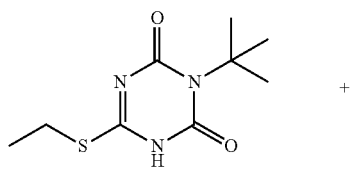

+

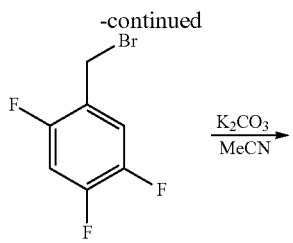

3-t-butyl-6-(ethylthio)-1,3,5-triazin-2,4(1H,3H)-dione (229.4 mg, 1.0 mmol), 2,4,5-trifluorobenzyl bromide (247.5 mg, 1.1 mmol) and potassium carbonate (165.8 mg, 1.2 mmol) were added to a reactor, dissolved in 20 mL of acetonitrile, heated to reflux and reacted for 3 hrs with stirring. The reaction was monitored by TLC. After the reaction was completed, the reaction solution was concentrated under reduced pressure to remove the solvent. The obtained solid residue was washed with a saturated aqueous sodium chloride solution, and extracted with ethyl acetate. The organic phase was collected and separated and purified by column chromatography (mobile phase: petroleum ether: ethyl acetate (V:V)=3:1), and dried to obtain Compound a1 (337.8 mg, yield 89.82%).

(2) Preparation of Compound c1

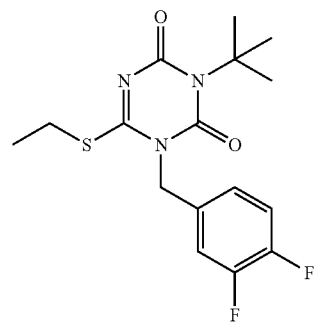

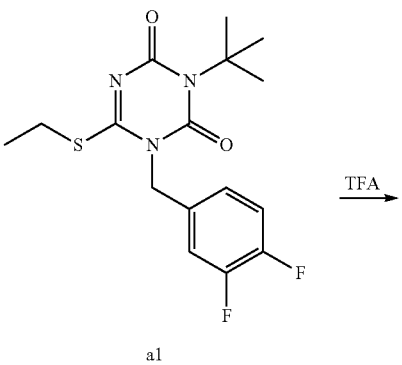

a1

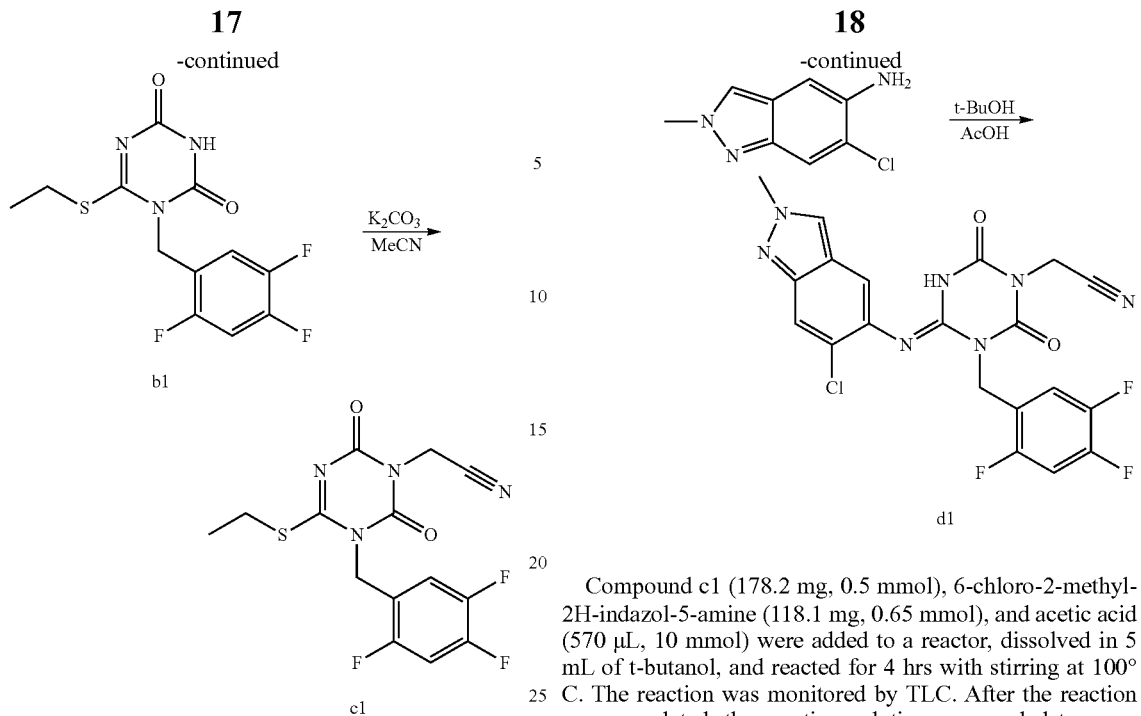

Step I: Synthesis of Compound b1

The obtained Compound a1 (373.4 mg, 1 mmol) was added to a reactor, 5 mL of trifluoroacetic acid (TFA) was added, and stirred overnight at room temperature. The system was then concentrated under reduced pressure by azeotropism with toluene, and dried to obtain Compound b1 (294.8 mg, yield 92.91%).

Step II: Synthesis of Compound c1

Compound b1 (317.3 mg, 1 mmol), bromoacetonitrile (85 μL, 1.2 mmol) and potassium carbonate (165.9 mg, 1.2 mmol) were added to a reactor, dissolved in 10 mL of acetonitrile, heated to reflux and reacted for 5 hrs with stirring. The reaction was monitored by TLC. After the reaction was completed, the obtained reaction solution was washed with a saturated aqueous sodium chloride solution, and extracted with ethyl acetate. The organic phase was collected and separated and purified by column chromatography (mobile phase: petroleum ether:ethyl acetate (V:V)=1:1), and dried to obtain Compound c1 (280.4 mg, yield 78.69%).

(3) Preparation of Compound d1

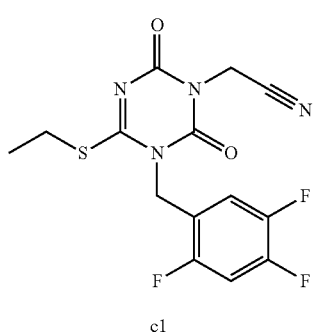

Compound c1 (178.2 mg, 0.5 mmol), 6-chloro-2-methyl-2H-indazol-5-amine (118.1 mg, 0.65 mmol), and acetic acid (570 μL, 10 mmol) were added to a reactor, dissolved in 5 mL of t-butanol, and reacted for 4 hrs with stirring at 100° C. The reaction was monitored by TLC. After the reaction was completed, the reaction solution was cooled to room temperature and concentrated under reduced pressure to remove the solvent. The residue was separated and purified by column chromatography (mobile phase: cyclohexane: ethyl acetate (V:V)=10:1), and dried to obtain Compound d1 (120.6 mg, yield 50.69%).

(4) Preparation of Compound 1

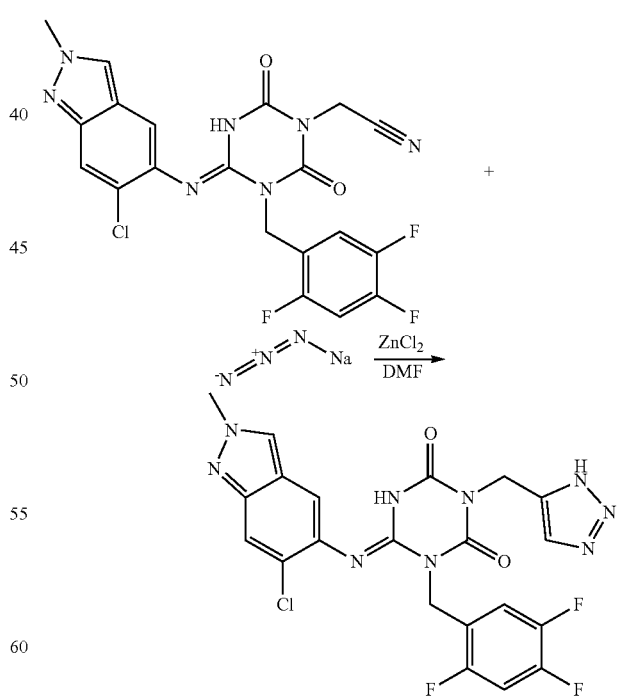

Figure 2:
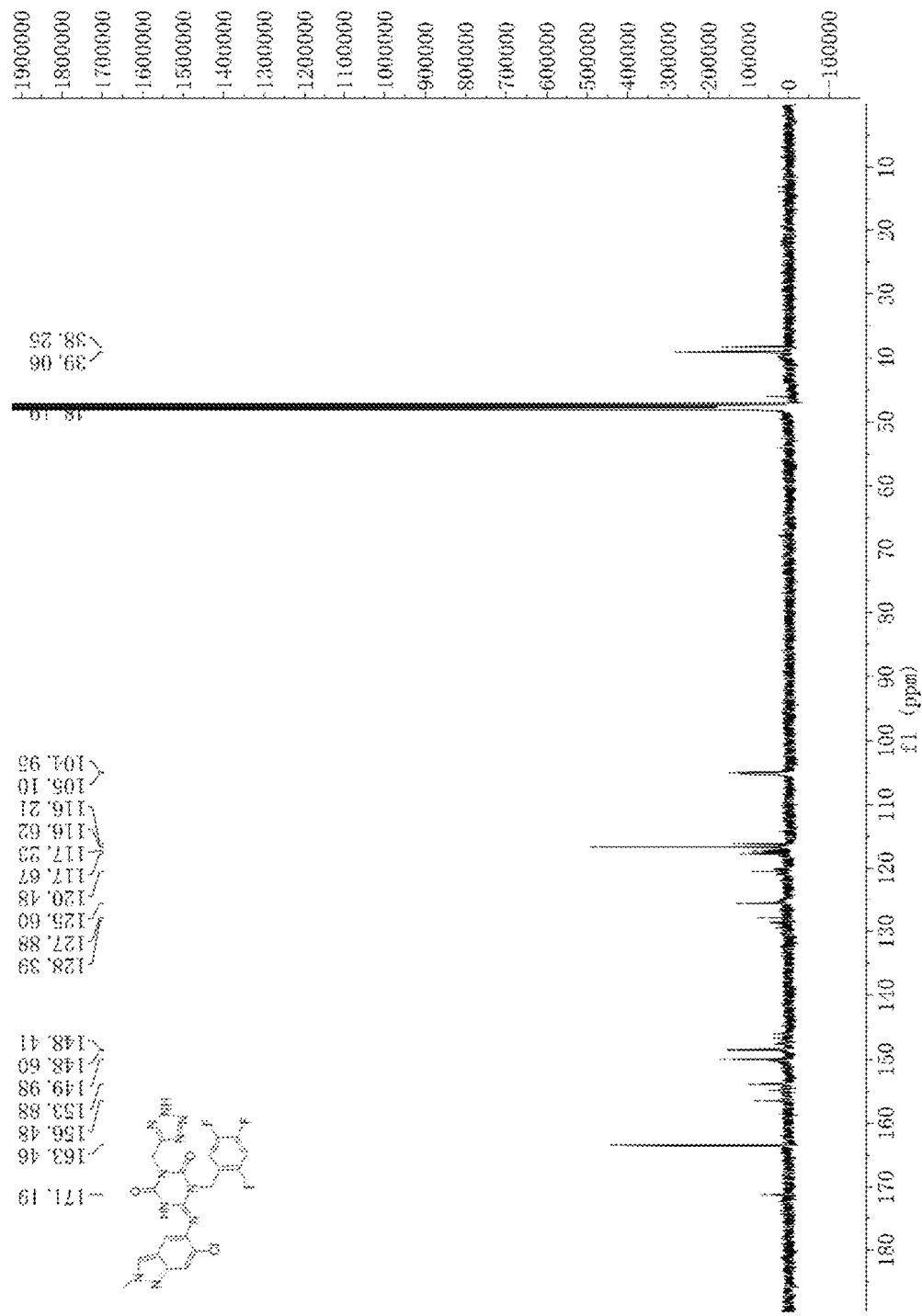
FIG. 2 is a $^{13}$C NMR spectrum of Compound 1 of the present invention in deuterated MeOD.
Figure 3:
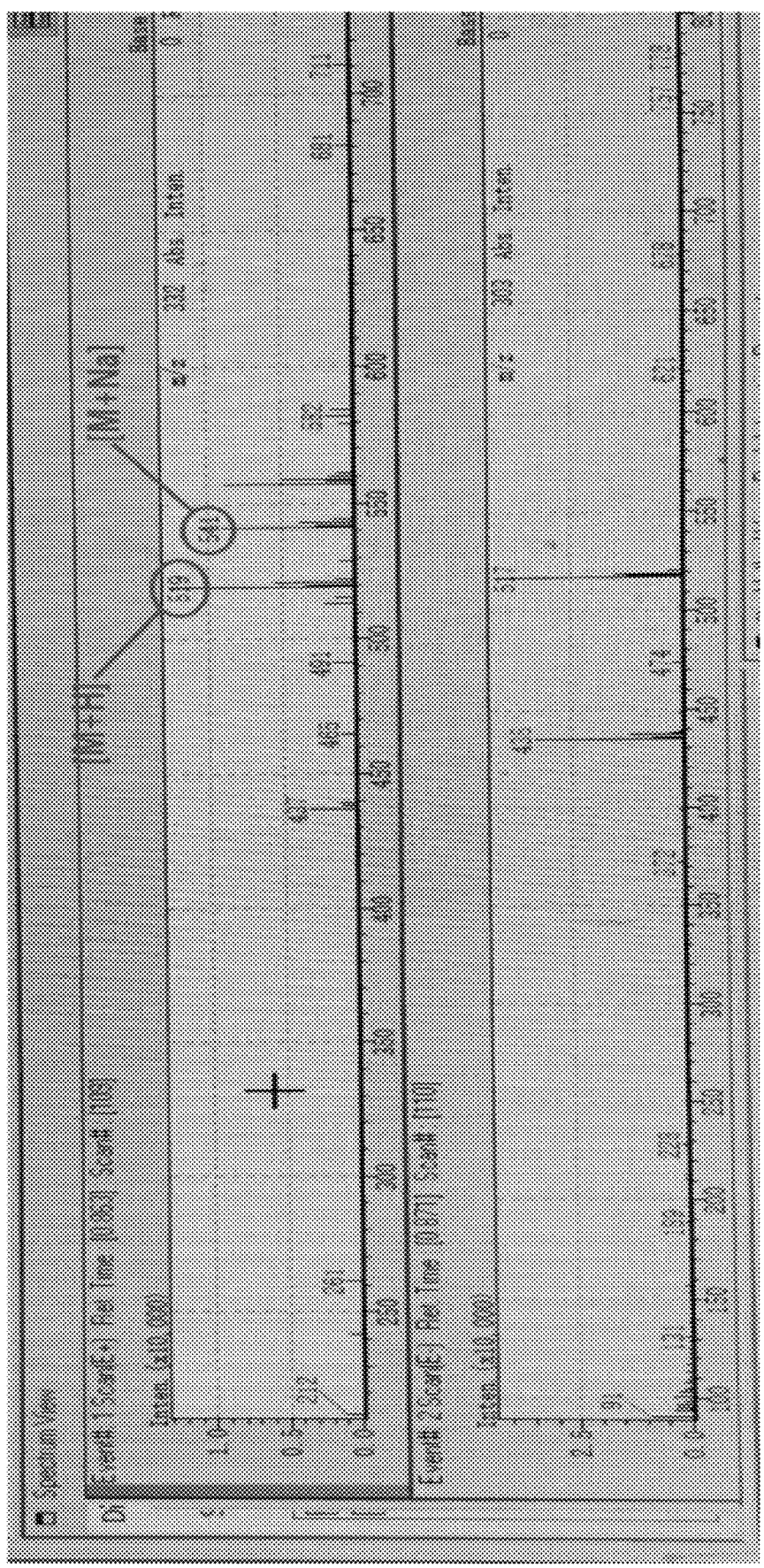
FIG. 3 is a MS spectrum of Compound 1 of the present invention.

Compound d1 (951.6 mg, 2 mmol), sodium azide (136.5 mg, 2.1 mmol), and zinc chloride (299.8 mg, 2.2 mmol) were added to a reactor, dissolved in 20 mL of N,N-dimethyl amide, heated to 95° C. under $N_2$ atmosphere, and reacted overnight with stirring. The reaction was monitored by TLC. After the reaction was completed, the reaction solution was cooled to room temperature. 20 mL of 2 M HCl solution was added to the reaction solution, and a solid was precipitated out. The solid was filtered out, and dried to obtain Compound 1 (361.12 mg, yield 34.80%). The $^1$H NMR spectrum of Compound 1 in deuterated MeOD is as shown in FIG. 1, the 13C NMR spectrum in deuterated MeOD is as shown in FIG. 2, and the MS spectrum is as shown in FIG. 3.

$^1$H NMR (600 MHz, MeOD) δ 8.16 (s, 1H), 8.02 (s, 1H), 7.73 (s, 1H), 7.60-7.49 (m, 1H), 7.26-7.12 (m, 1H), 5.42-5.36 (m, 4H), 4.21 (s, 3H).

$^{13}$C NMR (151 MHz, MeOD) δ 171.19, 163.46, 156.48, 153.88, 149.98, 148.60, 148.41, 128.39, 127.88, 125.60, 120.48, 117.67, 117.23, 116.62, 116.21, 105.10, 104.95, 48.19, 39.06, 38.25.

MS calcd for $C_{20}H_{14}ClF_3N_{10}O_2$, [M+H]$^+$: 519; found: 519.

MS calcd for $C_{20}H_{14}ClF_3N_{10}O_2$, [M+Na]$^+$: 541; found: 541.

Example 2

Preparation of Compound 2: (E)-3-((1H-tetrazol-5-yl)methyl)-1-benzyl-6-((6-chloro-2-methyl-2H-indazol-5-yl)imino)-1,3,5-triazin-2,4-dione

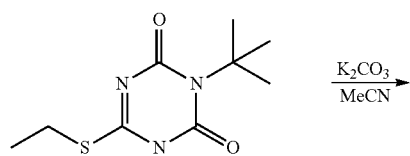

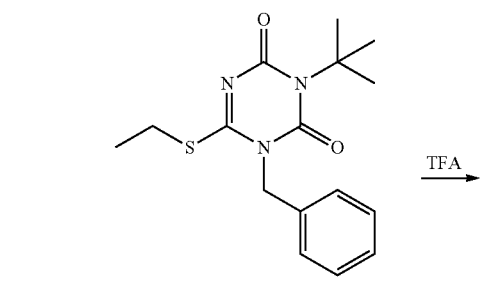

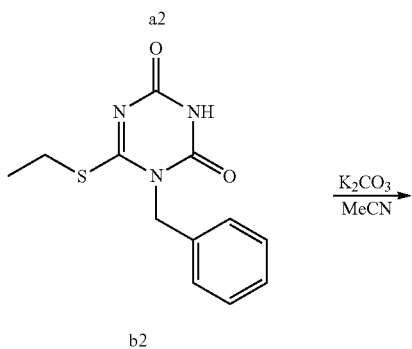

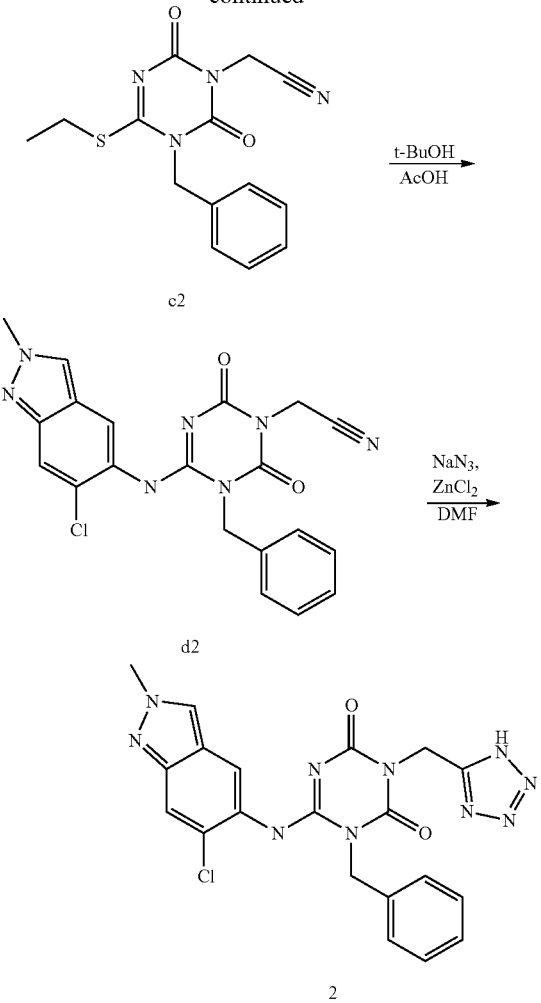

The preparation method was as described in Example 1, except that the corresponding raw materials were replaced. Yield of Compound 2 obtained: 30.54%.

$^1$H NMR (600 MHz, MeOD) δ 9.28 (s, 1H), 8.72 (s, 1H), 8.03 (s, 1H), 7.76-7.52 (m, 1H), 7.39-7.18 (m, 1H), 7.03 (s, 3H), 5.75-5.53 (m, 4H), 4.12 (s, 3H).

$^{13}$C NMR (151 MHz, MeOD) δ 169.42, 161.53, 155.73, 153.88, 149.58, 141.36, 139.75, 129.12, 125.94, 118.19, 115.47, 113.45, 112.53, 103.02, 101.87, 47.17, 38.56, 37.78.

MS calcd for $C_{20}H_{17}ClN_{10}O_2$, [M+H]$^+$: 465; found: 465.

Example 3

Preparation of Compound 3: (E)-3-(1H-tetrazol-5-yl)methyl)-6-(6-chloro-2-methyl-2H-indazol-5-yl)imino)-1-(4-methylbenzyl)-1,3,5-triazin-2,4-dione

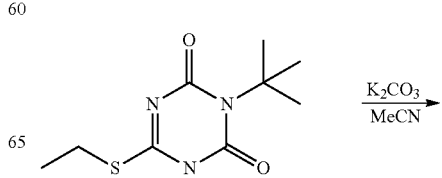

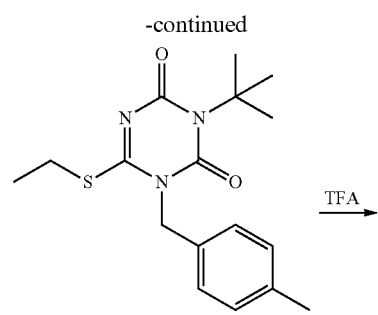
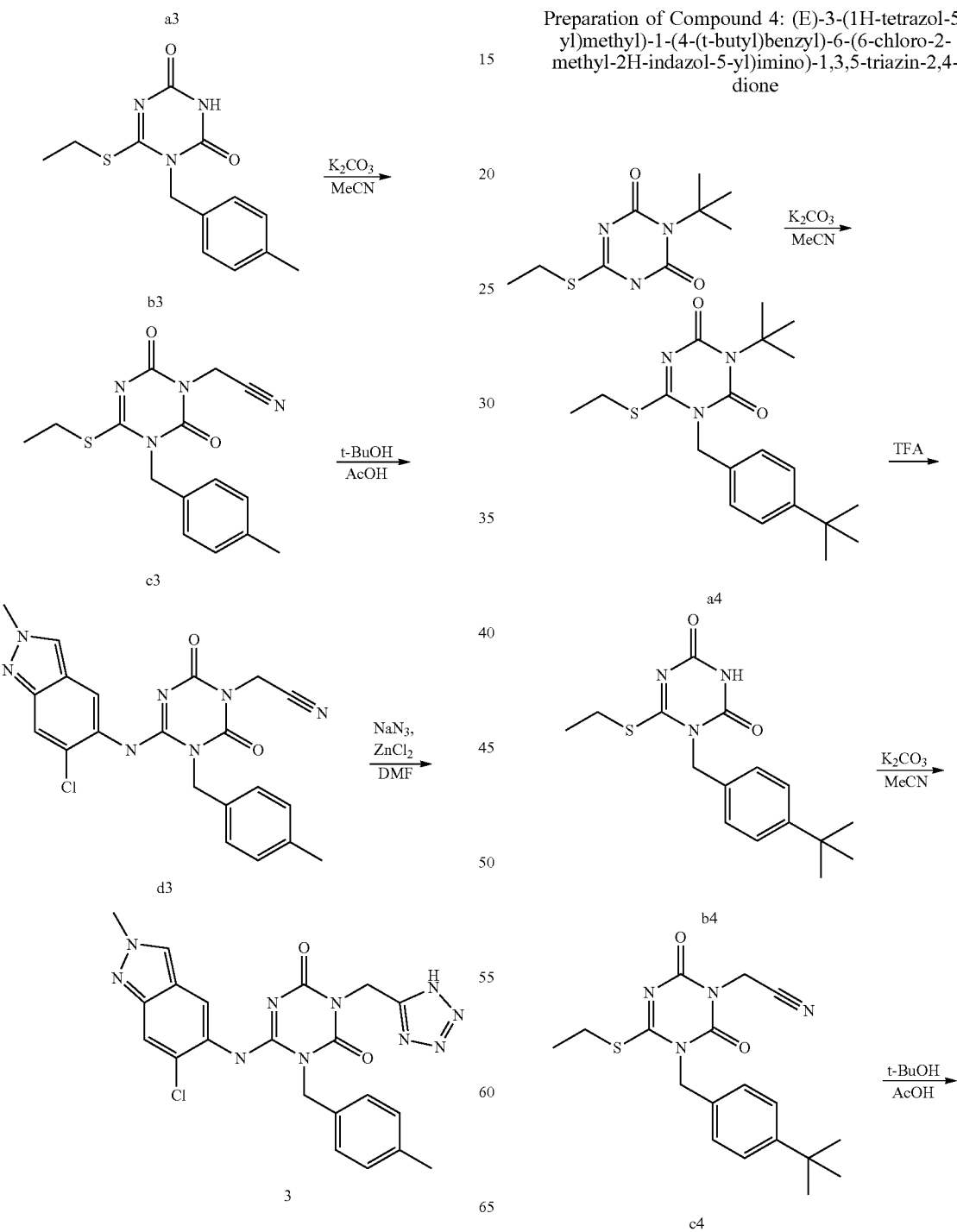
The preparation method was as described in Example 1, except that the corresponding raw materials were replaced. Yield of Compound 3 obtained: 35.23%.
$^1$H NMR (600 MHz, MeOD) δ 9.34 (s, 1H), 8.56 (s, 1H), 7.92 (s, 1H), 7.62 (m, 1H), 7.47-7.22 (m, 1H), 6.98 (s, 2H), 5.63-5.39 (m, 4H), 4.78 (s, 3H), 2.12 (s, 3H).
$^{13}$C NMR (151 MHz, MeOD) δ 168.13, 163.86, 153.77, 150.86, 147.67, 144.57, 138.67, 135.67, 123.67, 113.17, 111.67, 109.46, 105.84, 101.56, 47.67, 38.23, 35.13, 21.34.
MS calcd for $C_{21}H_{19}ClN_{10}O_2$, [M+H]$^+$: 479; found: 479.
Example 4
Preparation of Compound 4: (E)-3-(1H-tetrazol-5-yl)methyl)-1-(4-(t-butyl)benzyl)-6-(6-chloro-2-methyl-2H-indazol-5-yl)imino)-1,3,5-triazin-2,4-dione -continued

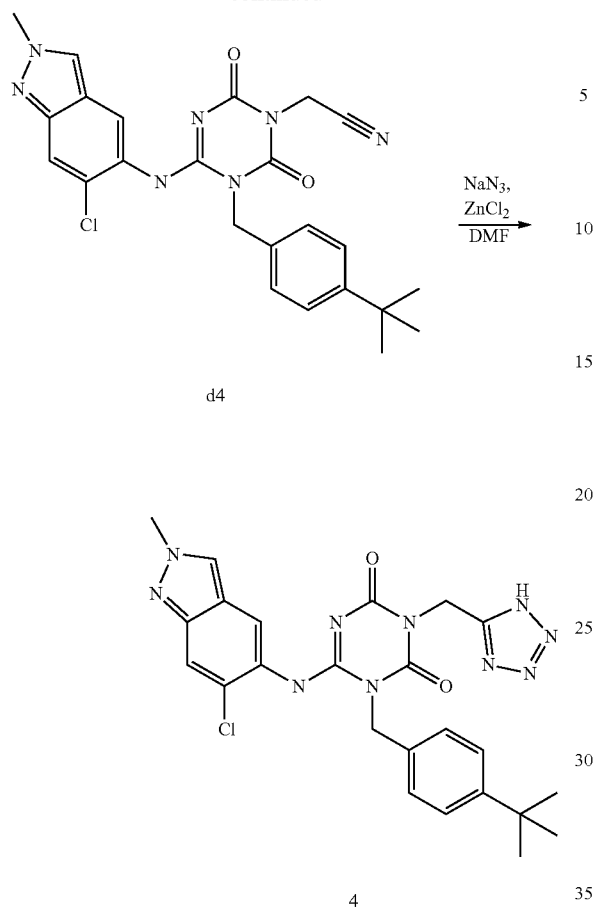

d4

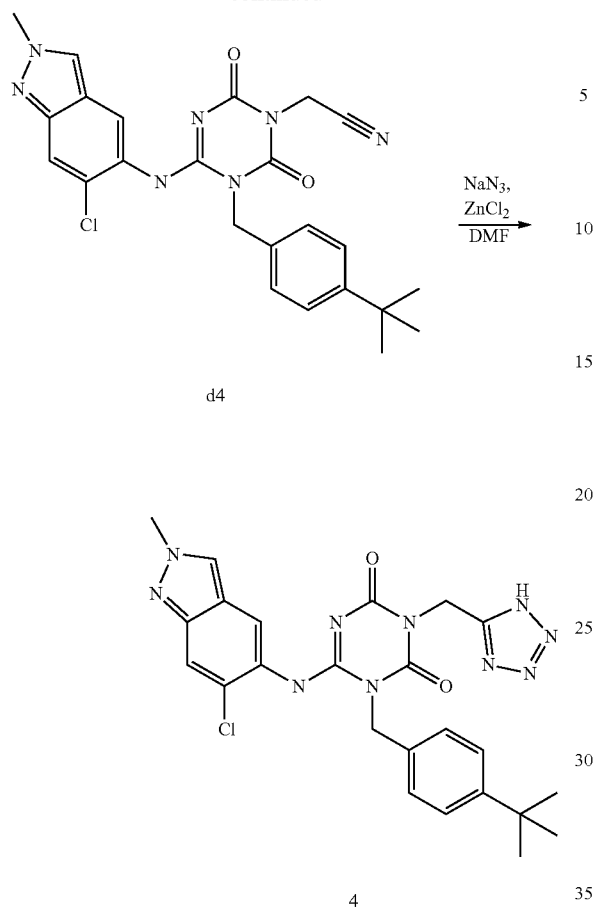

4

The preparation method was as described in Example 1, except that the corresponding raw materials were replaced. Yield of Compound 4 obtained: 36.35%.

$^1$H NMR (600 MHz, MeOD) δ 9.43 (s, 1H), 8.27 (s, 1H), 7.76 (s, 1H), 7.27-7.09 (m, 2H), 7.02 (m, 2H), 5.41-5.33 (m, 4H), 4.32 (s, 3H), 1.32 (s, 9H).

$^{13}$C NMR (151 MHz, MeOD) δ 168.25, 161.95, 152.36, 150.64, 144.38, 143.51, 138.86, 134.92, 124.57, 121.03, 117.51, 113.16, 110.87, 107.32, 105.54, 101.75, 46.53, 38.71, 35.20, 21.26.

MS calcd for $C_{24}H_{25}ClN_{10}O_2$, $[M+H]^+$: 521; found: 521.

Example 5

Preparation of Compound 5: (E)-3-(1H-tetrazol-5-yl)methyl)-6-(6-chloro-2-methyl-2H-indazol-5-yl)imino)-1-(4-chlorobenzyl)-1,3,5-triazin-2,4-dione

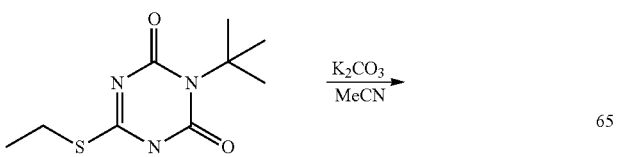

-continued

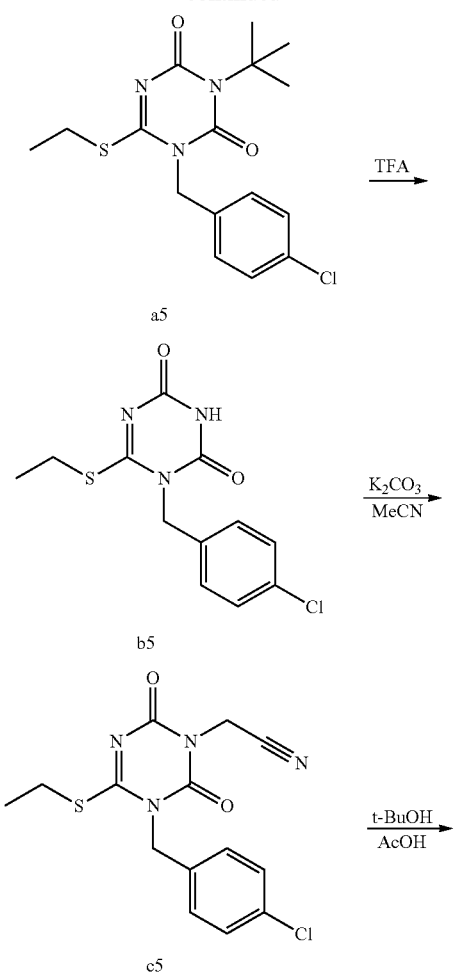

a5

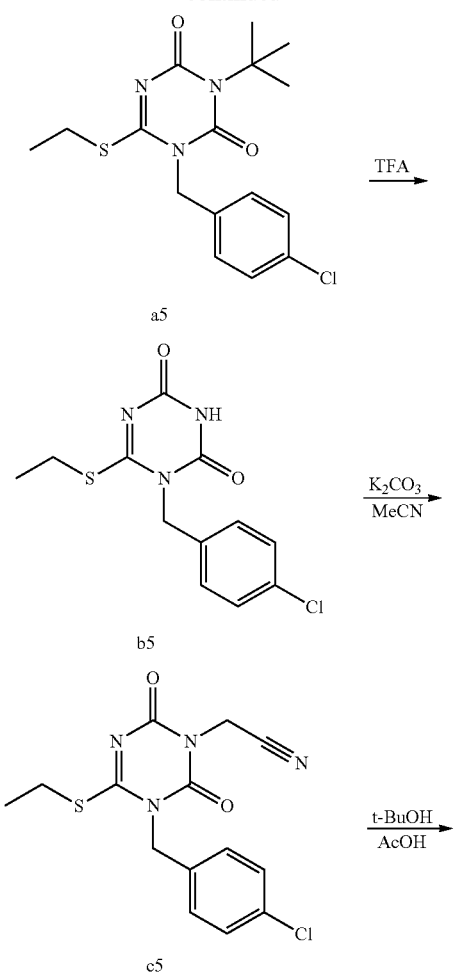

b5

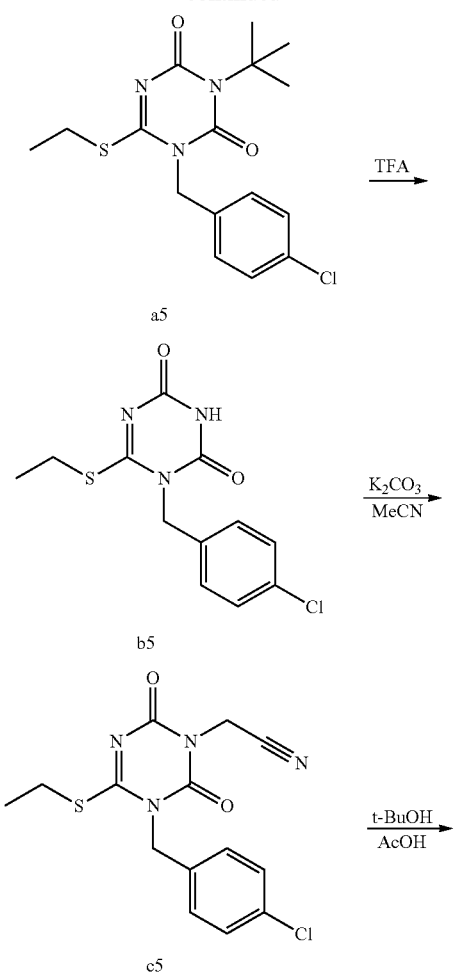

c5

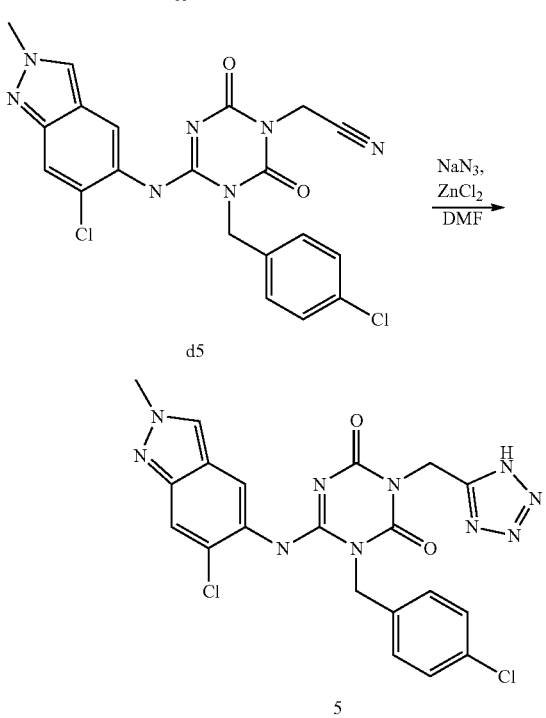

d5

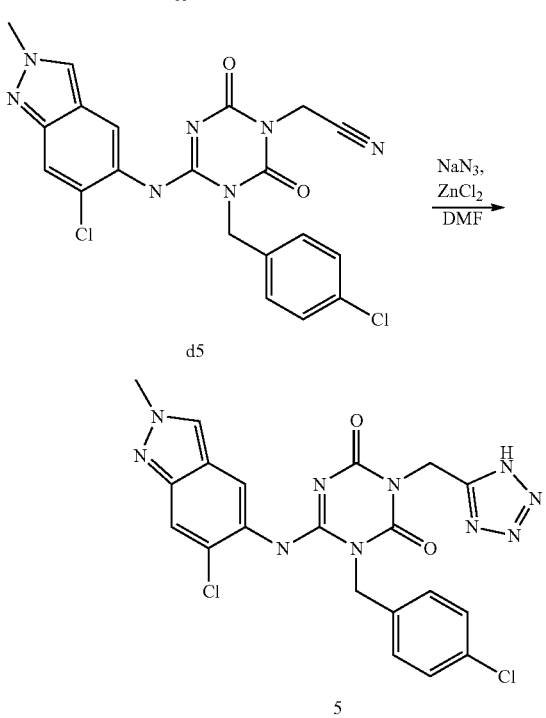

5

The preparation method was as described in Example 1, except that the corresponding raw materials were replaced. Yield of Compound 5 obtained: 39.82%.

$^1$H NMR (600 MHz, MeOD) δ 9.25 (s, 1H), 8.35 (s, 1H), 7.86 (s, 1H), 7.31-7.11 (m, 2H), 6.92 (m, 2H), 5.42-5.29 (m, 4H), 4.20 (s, 3H).

$^{13}$C NMR (151 MHz, MeOD) δ 167.36, 160.81, 151.33, 150.64, 144.48, 142.41, 137.87, 133.39, 125.56, 118.42, 113.21, 110.67, 106.93, 105.66, 100.75, 46.51, 42.20, 41.71.

MS calcd for $C_{20}H_{16}Cl_2N_{10}O_2$, [M+H]$^+$: 499; found: 499.

Example 6

Preparation of Compound 6: (E)-3-((1H-tetrazol-5-yl)methyl)-1-(4-bromophenyl)-6-((6-chloro-2-methyl-2H-indazol-5-yl)imino)-1,3,5-triazin-2,4-dione

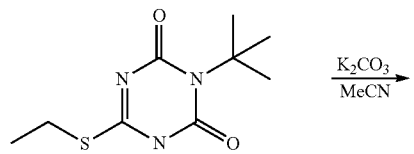

a6

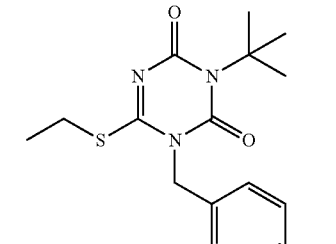

b6

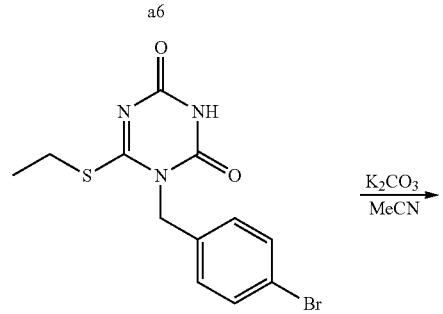

c6

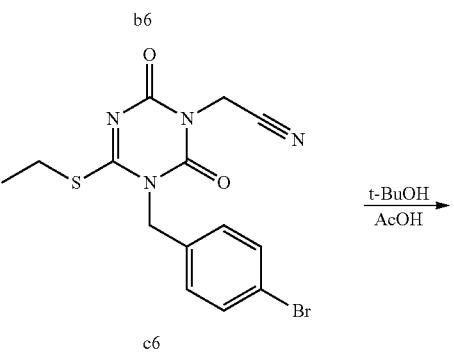

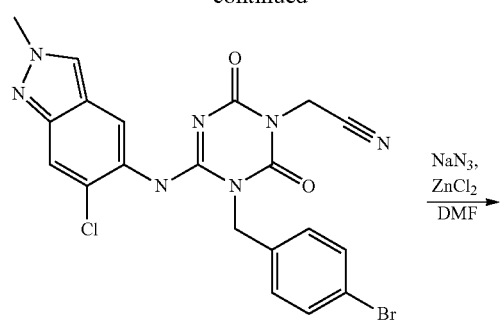

d6

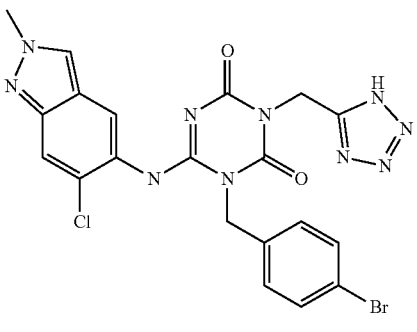

6

The preparation method was as described in Example 1, except that the corresponding raw materials were replaced. Yield of Compound 6 obtained: 41.23%.

$^1$H NMR (600 MHz, MeOD) δ 9.31 (s, 1H), 8.37 (s, 1H), 7.85 (s, 1H), 7.28-7.08 (m, 2H), 6.89 (m, 2H), 5.52-5.39 (m, 4H), 4.41 (s, 3H).

$^{13}$C NMR (151 MHz, MeOD) δ 168.37, 161.28, 150.56, 149.26, 143.47, 141.96, 137.78, 133.41, 124.85, 117.81, 114.01, 110.97, 106.36, 105.68, 100.52, 46.17, 42.53, 40.85.

MS calcd for $C_{20}H_{16}BrClN_{10}O_2$, [M+H]$^+$: 543; found: 543.

Example 7

Preparation of Compound 7: (E)-3-((1H-tetrazol-5-yl)methyl)-1-([1,1-biphenyl]-4-ylmethyl)-6-((6-chloro-2-methyl-2H-indazol-5-yl)imino)-1,3,5-triazin-2,4-dione

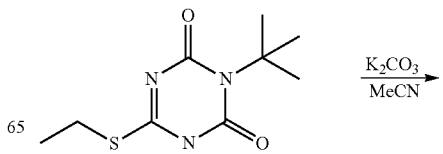

27

-continued

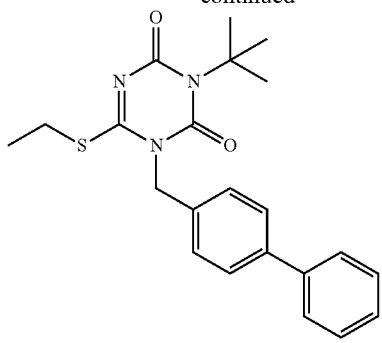

a7

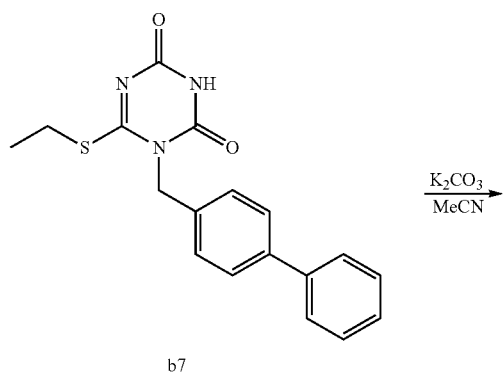

b7

28

-continued

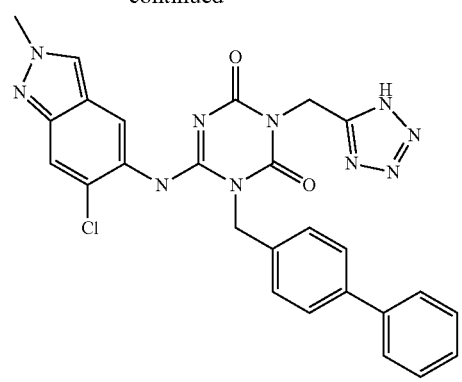

7

The preparation method was as described in Example 1, except that the corresponding raw materials were replaced. Yield of Compound 7 obtained: 32.51%.

$^1$H NMR (600 MHz, MeOD) δ 9.29 (s, 1H), 8.42 (s, 1H), 7.69 (s, 1H), 7.60-7.44 (m, 7.29-7.01 (m, 2H), 6.85 (m, 2H), 5.68-5.33 (m, 4H), 4.20 (s, 3H).

$^{13}$C NMR (151 MHz, MeOD) δ 167.41, 161.27, 149.56, 148.23, 144.36, 141.99, 141.36, 138.75, 132.81, 129.31, 127.62, 127.28, 123.95, 116.81, 113.03, 110.85, 106.76, 105.87, 100.44, 46.27, 42.45, 40.70.

MS calcd for $C_{26}H_{21}ClN_{10}O_2$, [M+H]$^+$: 541; found: 541.

Example 8

Preparation of Compound 8: (E)-3-(1H-tetrazol-5-yl)methyl)-6-((6-chloro-2-methyl-2H-indazol-5-yl)imino)-1-(4-(trifluoromethyl)benzyl)-1,3,5-triazin-2,4-dione

29
-continued

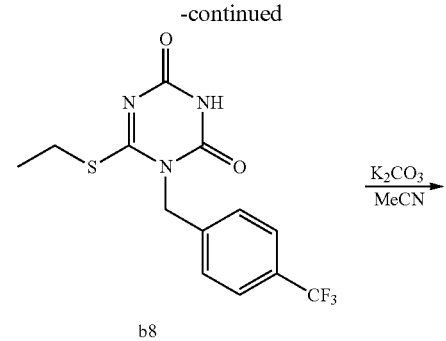
b8

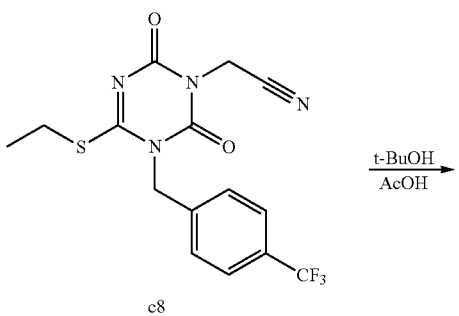
c8

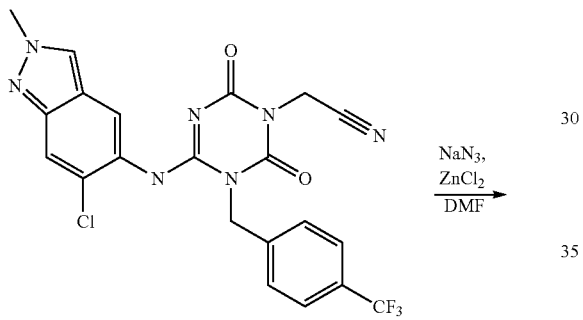
d8

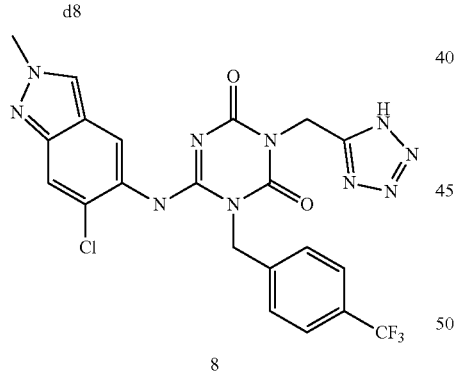
8

The preparation method was as described in Example 1, except that the corresponding raw materials were replaced. Yield of Compound 8 obtained: 33.54%.

$^1$H NMR (600 MHz, MeOD) δ 9.23 (s, 1H), 8.38 (s, 1H), 7.86 (s, 1H), 7.22-7.01 (m, 2H), 6.84 (m, 2H), 5.51-5.37 (m, 4H), 4.31 (s, 3H).

$^{13}$C NMR (151 MHz, MeOD) δ 167.38, 162.27, 151.54, 148.25, 143.52, 141.85, 137.76, 133.33, 124.75, 124.11, 117.88, 114.00, 110.94, 106.35, 105.53, 100.58, 46.26, 42.48, 40.76.

MS calcd for $C_{21}H_{16}ClF_3N_{10}O_2$, [M+H]$^+$: 533; found: 533.

30

Example 9

Preparation of Compound 9: (E)-3-(1H-tetrazol-5-yl)methyl)-6-(6-chloro-2-methyl-2H-indazol-5-yl)imino)-1-(4-nitrobenzyl)-1,3,5-triazin-2,4-dione

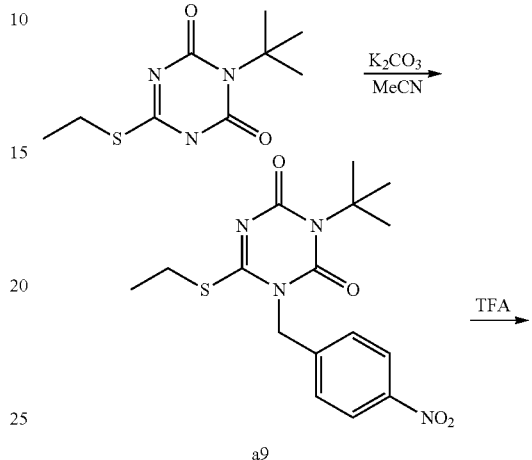
a9

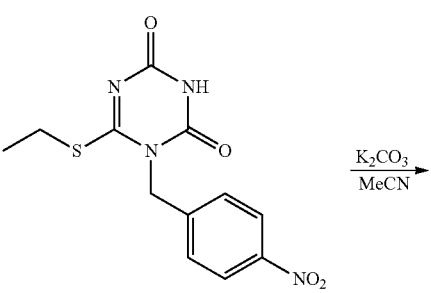
b9

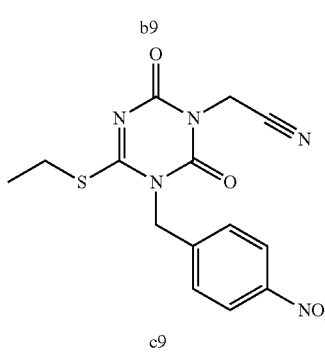
c9

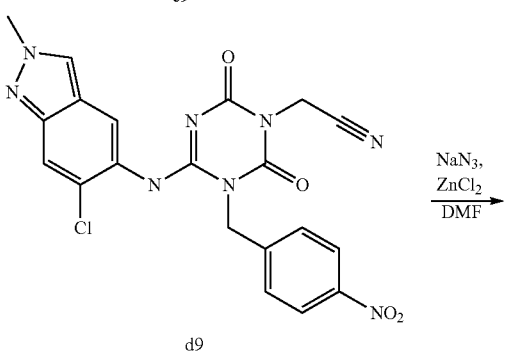
d9

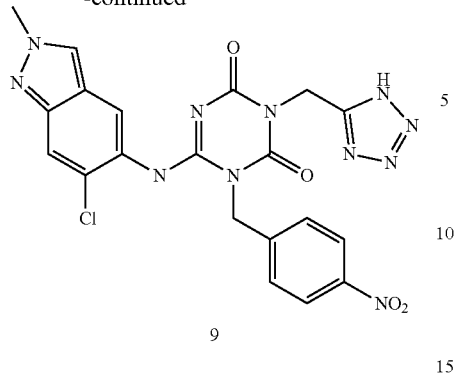

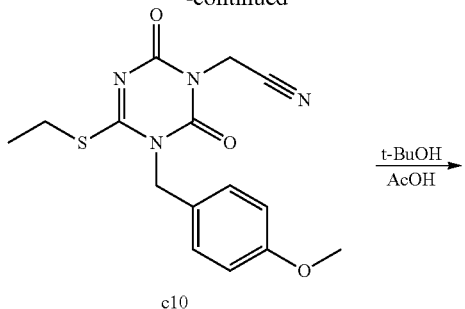

The preparation method was as described in Example 1, except that the corresponding raw materials were replaced. Yield of Compound 9 obtained: 29.68%.

$^1$H NMR (600 MHz, MeOD) δ 9.55 (s, 1H), 8.57 (s, 1H), 7.94 (s, 1H), 7.39-7.11 (m, 2H), 6.85 (m, 2H), 5.48-5.34 (m, 4H), 4.37 (s, 3H).

$^{13}$C NMR (151 MHz, MeOD) δ 168.38, 161.22, 150.45, 149.15, 143.38, 141.88, 137.99, 133.25, 124.84, 117.83, 113.97, 110.95, 106.56, 105.65, 100.58, 46.58, 42.42, 40.77.

MS calcd for $C_{20}H_{16}ClN_{11}O_4$, [M+H]$^+$: 510; found: 510.

Example 10

Preparation of Compound 10: (E)-3-(1H-tetrazol-5-yl)methyl)-6-(6-chloro-2-methyl-2H-indazol-5-yl)imino)-1-(4-methoxybenzyl)-1,3,5-triazin-2,4-dione

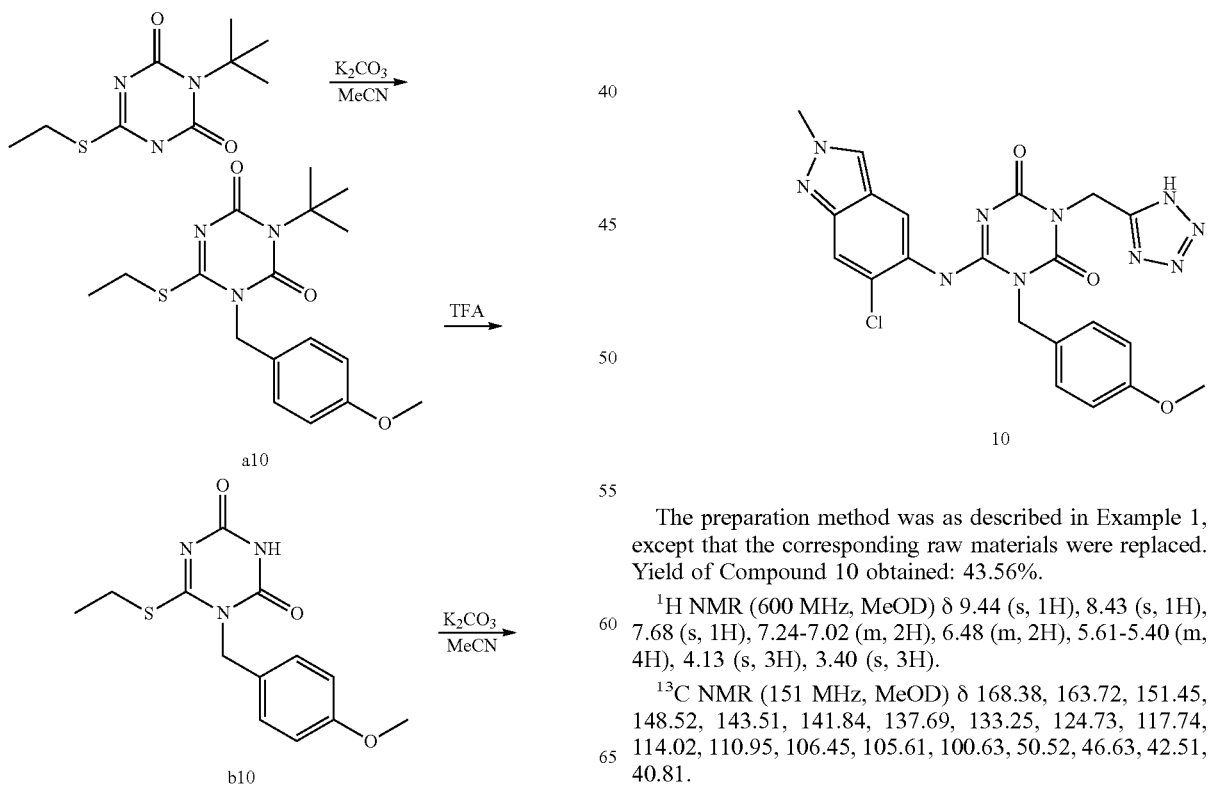

The preparation method was as described in Example 1, except that the corresponding raw materials were replaced. Yield of Compound 10 obtained: 43.56%.

$^1$H NMR (600 MHz, MeOD) δ 9.44 (s, 1H), 8.43 (s, 1H), 7.68 (s, 1H), 7.24-7.02 (m, 2H), 6.48 (m, 2H), 5.61-5.40 (m, 4H), 4.13 (s, 3H), 3.40 (s, 3H).

$^{13}$C NMR (151 MHz, MeOD) δ 168.38, 163.72, 151.45, 148.52, 143.51, 141.84, 137.69, 133.25, 124.73, 117.74, 114.02, 110.95, 106.45, 105.61, 100.63, 50.52, 46.63, 42.51, 40.81.

MS calcd for $C_{21}H_{19}ClN_{10}O_3$, [M+H]$^+$: 495; found: 495.

Example 11

Preparation of Compound 11: (E)-3-(1H-tetrazol-5-yl)methyl)-6-(6-chloro-2-methyl-2H-indazol-5-yl)imino)-1-(4-(trifluoromethoxy)benzyl)-1,3,5-triazin-2,4-dione

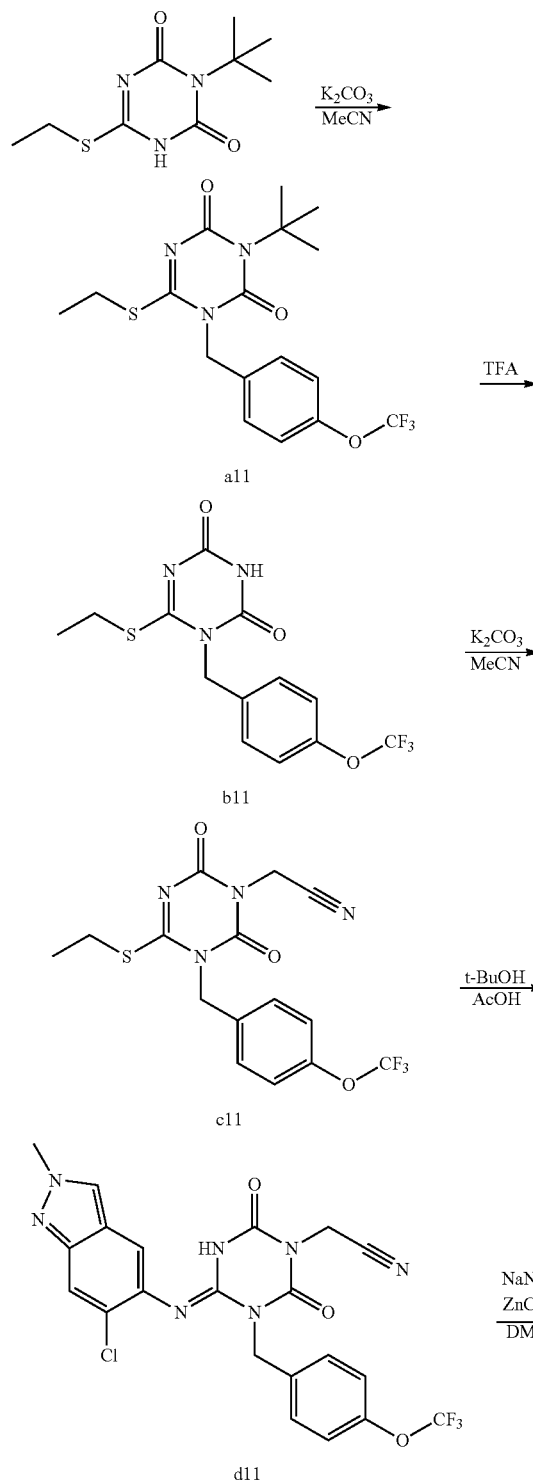

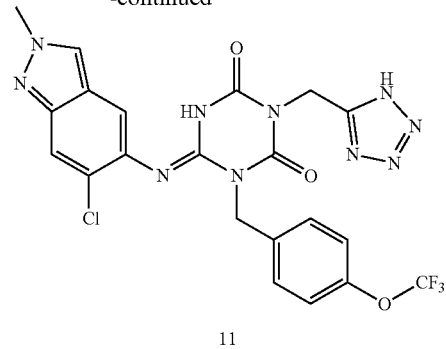

The preparation method was as described in Example 1, except that the corresponding raw materials were replaced. Yield of Compound 11 obtained: 39.27%.

$^1$H NMR (600 MHz, MeOD) δ 9.39 (s, 1H), 8.41 (s, 1H), 7.69 (s, 1H), 7.53-7.21 (m, 2H), 6.50 (m, 2H), 5.57-5.39 (m, 4H), 4.22 (s, 3H).

$^{13}$C NMR (151 MHz, MeOD) δ 168.65, 163.75, 151.43, 148.51, 143.42, 141.52, 137.66, 132.97, 128.92, 124.53, 117.46, 114.00, 110.51, 106.45, 105.16, 100.36, 46.52, 42.26, 40.53.

MS calcd for $C_{21}H_{16}ClF_3N_{10}O_3$, [M+H]$^+$: 549; found: 549.

Example 12

Preparation of Compound 12: E)-3-(1H-tetrazol-5-yl)methyl)-6-(6-chloro-2-methyl-2H-indazol-5-yl)imino)-1-(4-fluorobenzyl)-1,3,5-triazin-2,4-dione

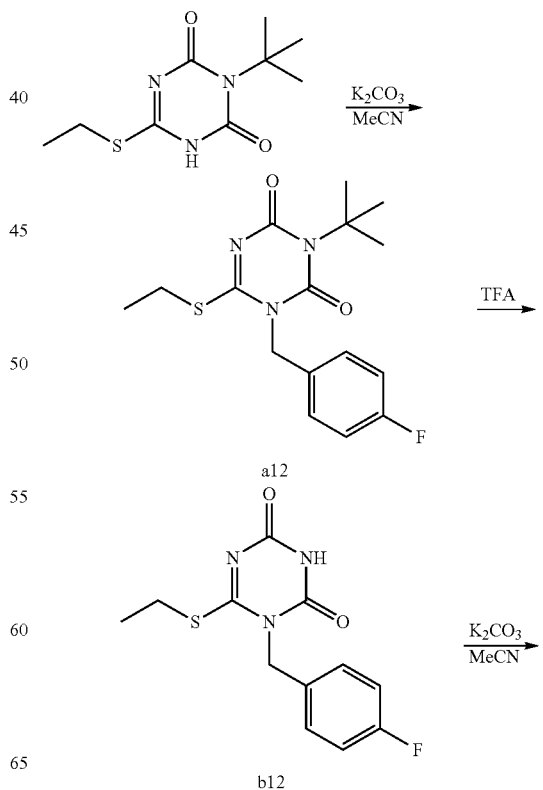

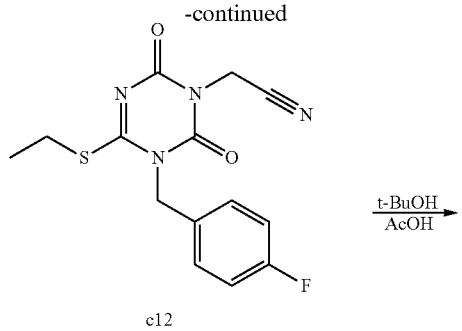
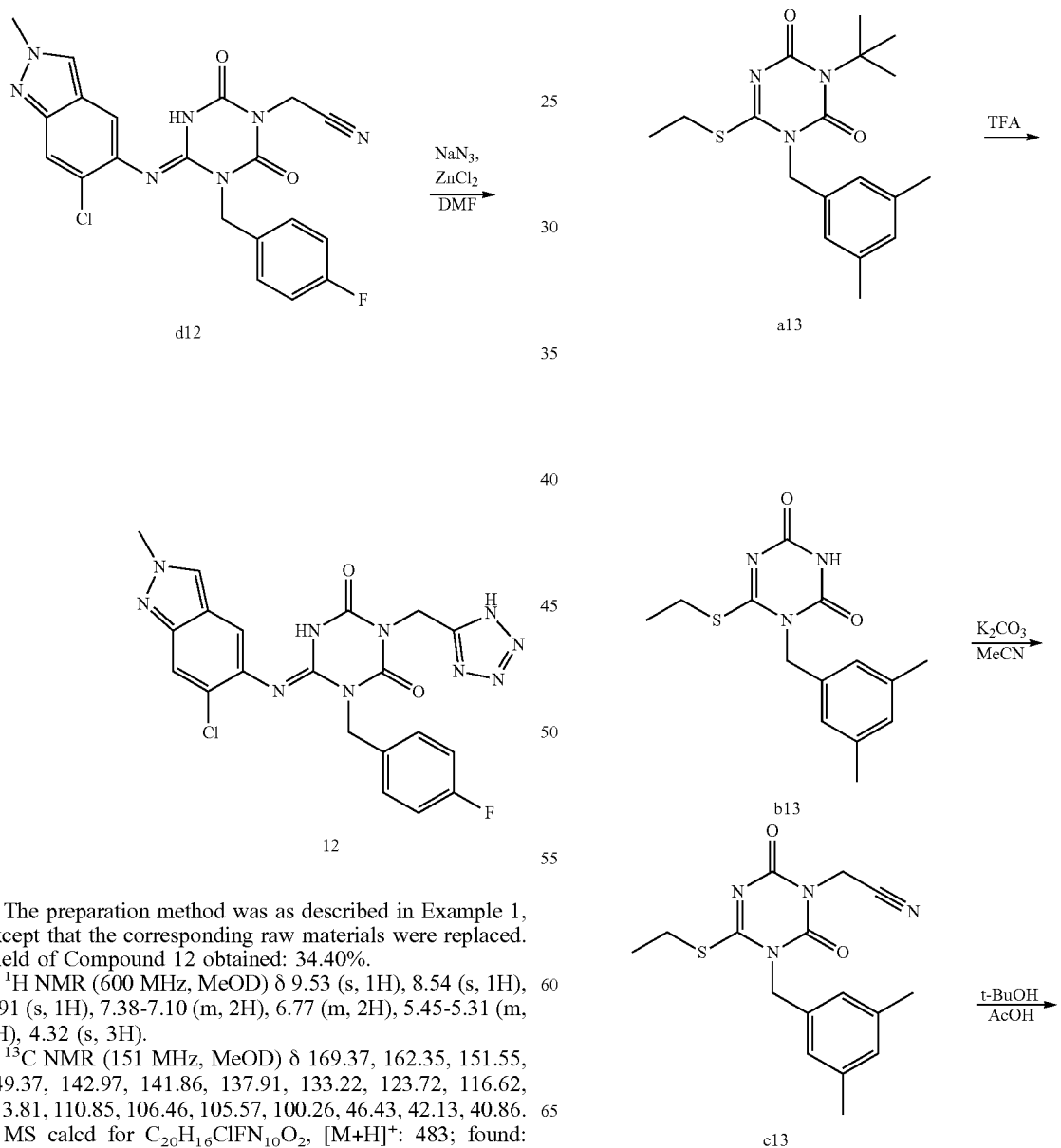
The preparation method was as described in Example 1, except that the corresponding raw materials were replaced. Yield of Compound 12 obtained: 34.40%.
$^{1}$H NMR (600 MHz, MeOD) δ 9.53 (s, 1H), 8.54 (s, 1H), 7.91 (s, 1H), 7.38-7.10 (m, 2H), 6.77 (m, 2H), 5.45-5.31 (m, 4H), 4.32 (s, 3H).
$^{13}$C NMR (151 MHz, MeOD) δ 169.37, 162.35, 151.55, 149.37, 142.97, 141.86, 137.91, 133.22, 123.72, 116.62, 113.81, 110.85, 106.46, 105.57, 100.26, 46.43, 42.13, 40.86.
MS calcd for $C_{20}H_{16}ClFN_{10}O_2$, [M+H]$^+$: 483; found: 483.
Example 13
Preparation of Compound 13: (E)-3-(1H-tetrazol-5-yl)methyl)-6-(6-chloro-2-methyl-2H-indazol-5-yl)imino)-1-(3,5-dimethyl benzyl)-1,3,5-triazin-2,4-dione

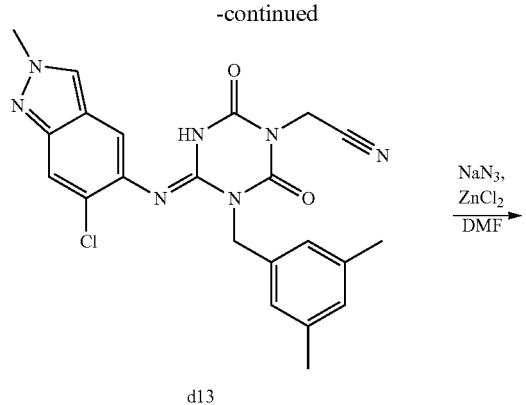
d13
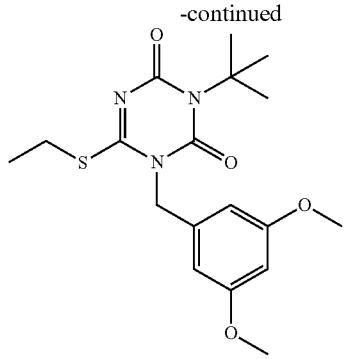
a14
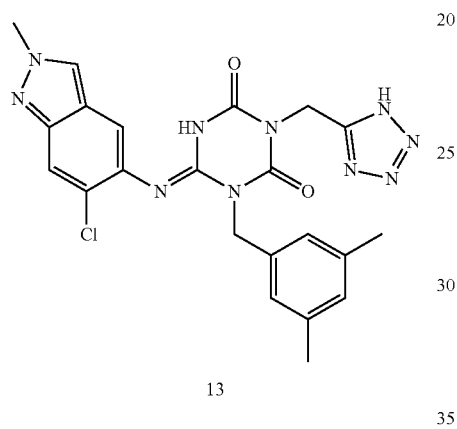
13
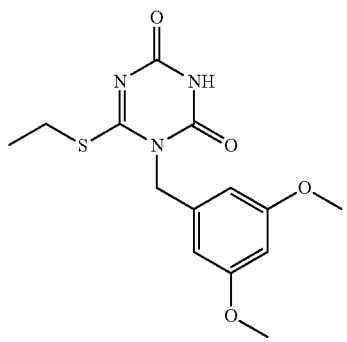
b14
The preparation method was as described in Example 1, except that the corresponding raw materials were replaced. Yield of Compound 13 obtained: 36.44%.
$^1$H NMR (600 MHz, MeOD) δ 9.51 (s, 1H), 8.50 (s, 1H), 7.85 (s, 1H), 7.39-7.12 (m, 3H), 5.42-5.30 (m, 4H), 4.21 (s, 3H), 2.09 (s, 6H).
$^{13}$C NMR (151 MHz, MeOD) δ 170.41, 162.42, 151.38, 149.25, 143.02, 141.54, 137.93, 133.23, 123.77, 116.28, 113.65, 110.88, 106.35, 105.82, 100.24, 46.50, 42.19, 40.84, 21.90.
MS calcd for $C_{22}H_{21}ClN_{10}O_2$, $[M+H]^+$: 493; found: 493.
Example 14
Preparation of Compound 14: (E)-3-(1H-tetrazol-5-yl)methyl)-6-(6-chloro-2-methyl-2H-indazol-5-yl)imino)-1-(3,5-dimethoxybenzyl)-1,3,5-triazin-2,4-dione
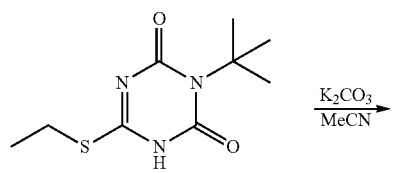
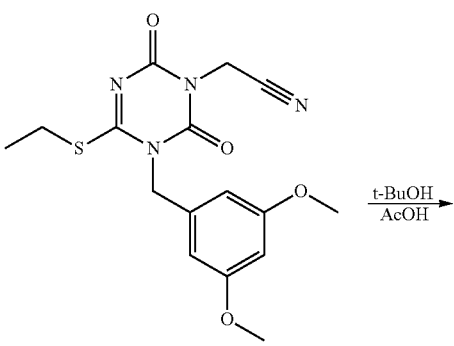
c14
d14

-continued

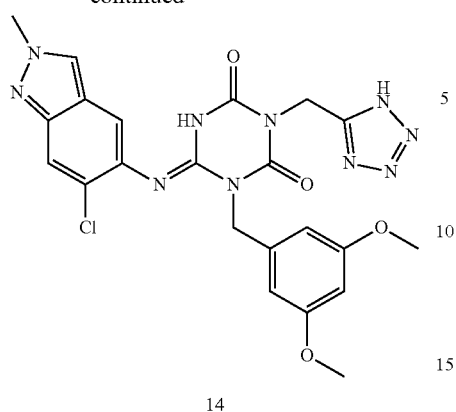

14

The preparation method was as described in Example 1, except that the corresponding raw materials were replaced. Yield of Compound 14 obtained: 42.49%.

$^1$H NMR (600 MHz, MeOD) δ 9.48 (s, 1H), 8.34 (s, 1H), 7.76 (s, 1H), 7.41-7.23 (m, 3H), 5.41-5.31 (m, 4H), 4.13 (s, 3H), 3.82 (s, 6H).

$^{13}$C NMR (151 MHz, MeOD) δ 171.53, 161.73, 161.44, 155.87, 153.85, 149.63, 141.12, 139.63, 128.19, 118.47, 115.54, 113.53, 112.02, 103.78, 101.08, 55.71, 47.65, 38.98, 37.87.

MS calcd for $C_{22}H_{21}ClN_{10}O_4$, [M+H]$^+$: 525; found: 525.

Example 15

Preparation of Compound 15: (E)-3-(1H-tetrazol-5-yl)methyl)-6-(6-chloro-2-methyl-2H-indazol-5-yl)imino)-1-(3,5-difluorobenzyl)-1,3,5-triazin-2,4-dione

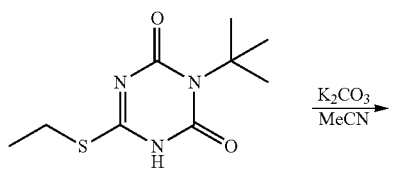

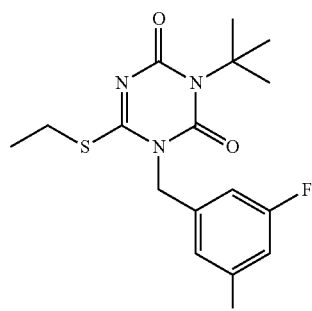

a15

-continued

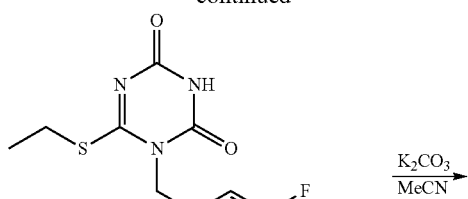

b15

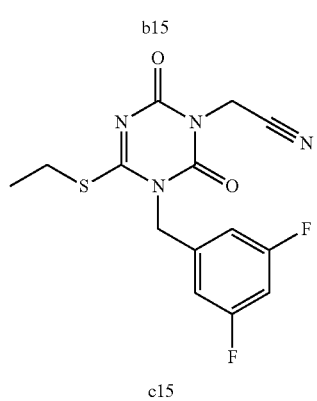

c15

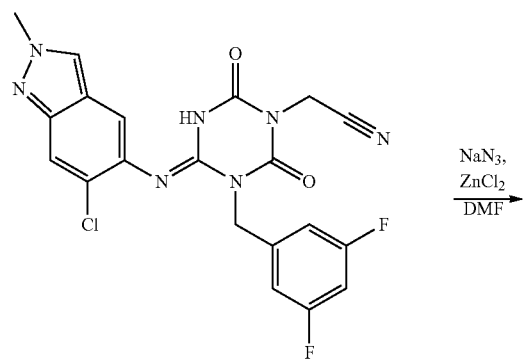

d15

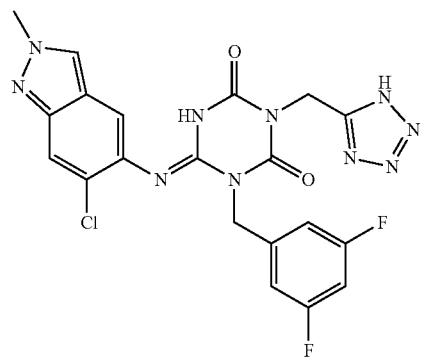

15

The preparation method was as described in Example 1, except that the corresponding raw materials were replaced. Yield of Compound 15 obtained: 42.68%.

$^1$H NMR (600 MHz, MeOD) δ 9.58 (s, 1H), 8.21 (s, 1H), 7.68 (s, 1H), 7.42-7.19 (m, 3H), 5.29-5.18 (m, 4H), 4.12 (s, 3H).

$^{13}$C NMR (151 MHz, MeOD) δ 172.51, 162.17, 161.43, 155.56, 152.87, 149.23, 141.79, 138.56, 127.18, 114.54, 112.23, 112.01, 102.97, 100.171, 55.47, 47.89, 38.15, 37.42.
MS calcd for $C_{20}H_{15}ClF_2N_{10}O_2$, $[M+H]^+$: 501; found: 501.

Example 16

Preparation of Compound 16: (E)-6-(6-chloro-2-methyl-2H-indazol-5-yl)imino)-3-(1-methyl-1H-tetrazol-5-yl)methyl)-1-(2,4,5-trifluorobenzyl)-1,3,5-triazin-2,4-dione (1) Preparation of Compound a16

The preparation method was the same as that in Example 1.

(2) Preparation of Compound c16

The preparation method was the same as that in Example 1.

(3) Preparation of Compound d16

The preparation method was the same as that in Example 1.

(4) Preparation of Compound e16

The preparation method was the same as that in Example 1.

(5) Preparation of Compound 16

In a glove box, bis(dibenzylideneacetone)palladium (6.9 mg, 0.012 mmol), 2-(di-t-butylphosphino)-3,6-dimethoxy-2'-4'-6'tri-1-propyl-1,1'-biphenyl (8.7 mg, 0.018 mmol), and potassium phosphate (95.5 mg, 0.45 mmol) were added to a reactor, and dissolved in 1.5 mL of 1,4-dioxane. The system was removed from the glove box, heated for 5 min at 120° C. with stirring, then cooled to room temperature, and transferred to the glove box. Methyl trifluoromethansulfonate (49.2 mg, 0.3 mmol) and Compound 1 (186.8 mg, 0.36 mmol) were added to the reactor, and reacted for 24 hrs at 70° C. with stirring. After the reaction was completed, the reaction solution was diluted with dichloromethane, and extracted. The organic phase was concentrated under reduced pressure, separated and purified by column chromatography (mobile phase: dichloromethane:methanol (V:V)=12:1), and dried to obtain Compound 16 (63.62 mg, yield 39.80%).

$^1$H NMR (600 MHz, MeOD) δ 8.17 (s, 1H), 8.01 (s, 1H), 7.72 (s, 1H), 7.61-7.44 (m, 1H), 7.25-7.01 (s, 1H), 5.41-5.32 (m, 4H), 4.19 (s, 3H), 3.75 (s, 3H).

$^{13}$C NMR (151 MHz, MeOD) δ 172.46, 163.23, 156.46, 153.62, 149.10, 148.55, 148.34, 128.88, 127.52, 125.64, 120.82, 117.32, 117.13, 116.25, 116.01, 105.12, 104.15, 48.18, 39.08, 38.21, 33.83.

MS calcd for $C_{21}H_{16}ClF_3N_{10}O_2$, $[M+H]^+$: 533; found: 533.

Example 17

Preparation of Compound 17: (E)-6-(6-chloro-2-methyl-2H-indazol-5-yl)imino)-3-(1-ethyl-1H-1,tetrazol-5-yl)methyl)-1-(2,4,5-trifluorobenzyl)-1,3,5-triazin-2,4-dione

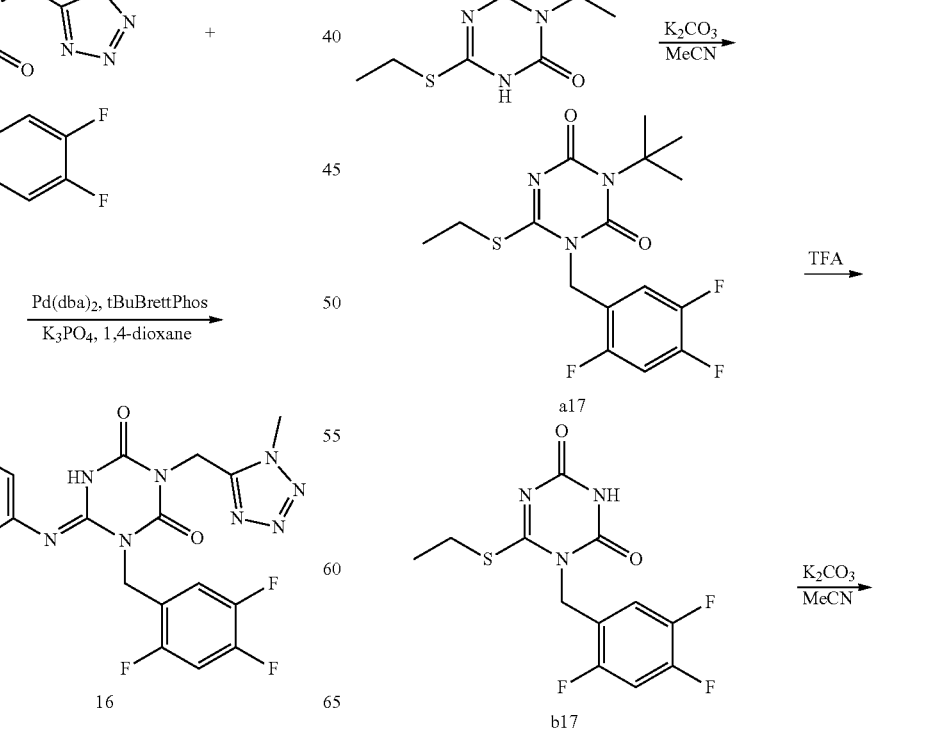

43

-continued

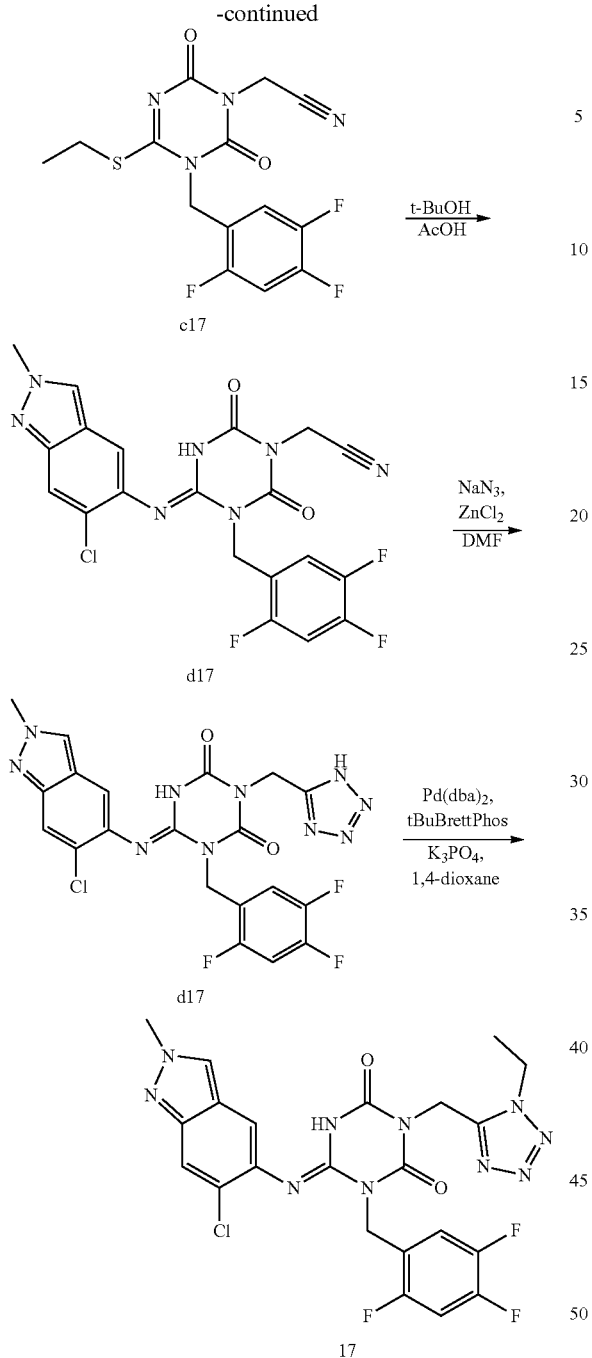

The preparation method was as described in Example 16, except that the corresponding raw materials were replaced. Yield of Compound 17 obtained: 31.25%.

$^1$H NMR (600 MHz, MeOD) δ 8.70 (s, 1H), 8.21 (s, 1H), 7.97 (s, 1H), 7.55-7.34 (m, 1H), 7.21-7.04 (s, 1H), 5.45-5.22 (m, 4H), 4.09 (s, 3H), 3.87 (s, 2H), 1.54 (s, 3H).

$^{13}$C NMR (151 MHz, MeOD) δ 171.42, 163.82, 156.31, 153.10, 149.12, 148.15, 148.38, 128.25, 127.46, 125.62, 120.87, 117.72, 117.15, 116.08, 115.89, 105.11, 104.25, 48.39, 39.17, 38.25, 33.86, 15.07.

MS calcd for $C_{22}H_{18}ClF_3N_{10}O_2$, [M+H]$^+$: 547; found: 547.

44

Example 18

Preparation of Compound 18: (E)-6-(6-chloro-2-methyl-2H-indazol-5-yl)imino)-3-(1-ethyl-1H-tetrazol-5-yl)methyl)-1-(4-(trifluoromethyl)benzyl)-1,3,5-triazin-2,4-dione

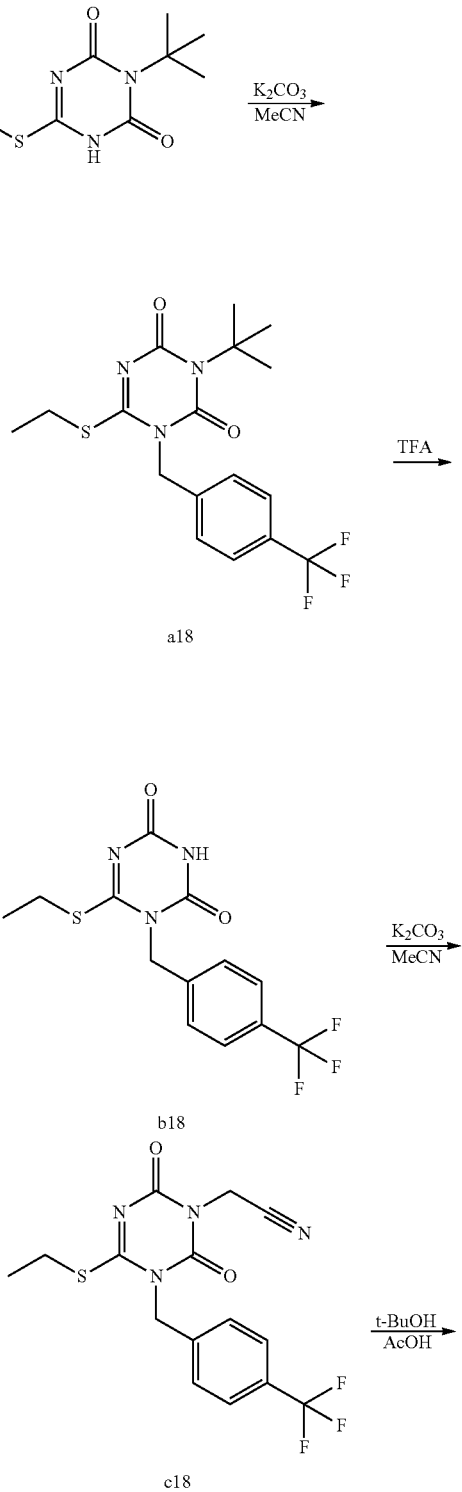

-continued

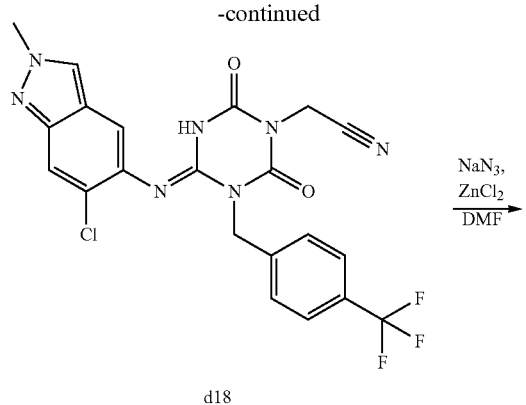

d18 e18

18

The preparation method was as described in Example 16, except that the corresponding raw materials were replaced. Yield of Compound 18 obtained: 33.85%.

$^1$H NMR (600 MHz, MeOD) δ 9.34 (s, 1H), 8.37 (s, 1H), 7.85 (s, 1H), 7.25-7.11 (m, 2H), 6.74 (m, 2H), 5.73-5.57 (m, 4H), 4.30 (s, 3H), 3.95 (s, 2H), 1.54 (s, 3H).

$^{13}$C NMR (151 MHz, MeOD) δ 165.27, 162.26, 151.95, 148.54, 143.22, 141.25, 137.85, 133.63, 124.11, 124.02, 117.87, 114.05, 110.91, 106.33, 105.73, 100.57, 46.22, 42.87, 42.24, 40.09, 15.08.

MS calcd for $C_{23}H_{20}ClF_3N_{10}O_2$, [M+H]$^+$: 561; found: 561.

Example 19

Preparation of Compound 19: (E)-6-(2-methyl-2H-indazol-5-yl)imino)-3-(1-ethyl-1H-tetrazol-5-yl)methyl)-1-(4-nitrobenzyl)-1,3,5-triazin-2,4-dione

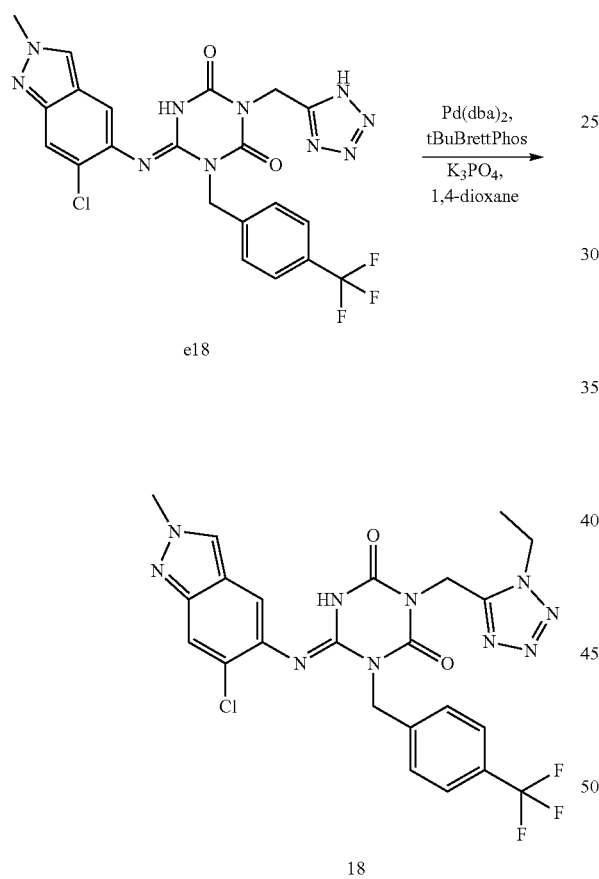

a19 b19 c19 d19

-continued

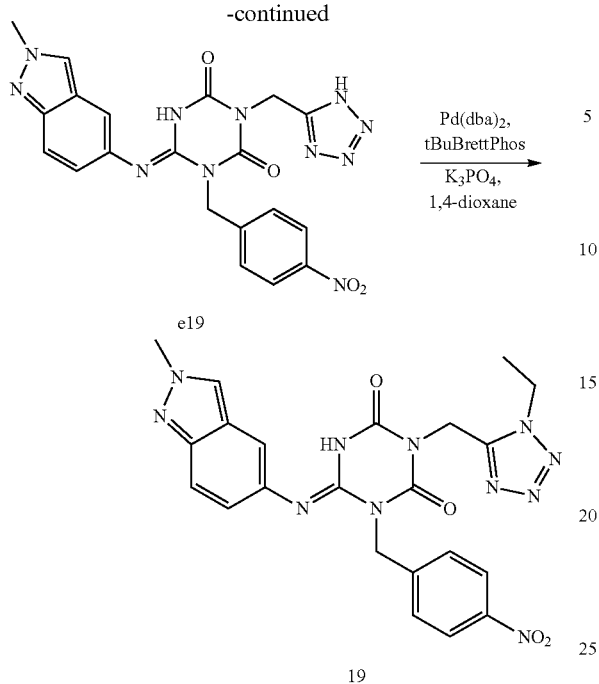

e19

19

The preparation method was as described in Example 16, except that the corresponding raw materials were replaced. Yield of Compound 19 obtained: 34.70%.

$^1$H NMR (600 MHz, MeOD) δ 9.74 (s, 1H), 8.45 (s, 1H), 7.74 (s, 1H), 7.31-7.08 (m, 2H), 6.44 (m, 2H), 5.81-5.56 (m, 4H), 4.31 (s, 3H), 3.94 (s, 2H), 1.53 (s, 3H).

$^{13}$C NMR (151 MHz, MeOD) δ 168.87, 161.21, 152.25, 148.58, 143.62, 141.26, 137.36, 133.15, 124.17, 124.01, 117.88, 113.14, 109.87, 105.32, 104.72, 100.86, 46.12, 42.77, 40.18, 14.97.

MS calcd for $C_{22}H_{21}N_{11}O_4$, [M+H]$^+$: 504; found: 504.

Example 20

Preparation of Compound 20: (E)-6-(6-chloro-2-methyl-2H-indazol-5-yl)imino)-3-(1-ethyl-1H-tetrazol-5-yl)methyl)-1-(4-chlorobenzyl)-1,3,5-triazin-2,4-dione

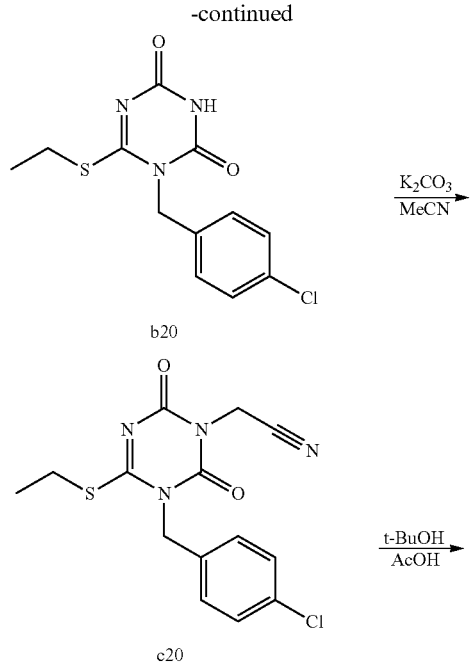

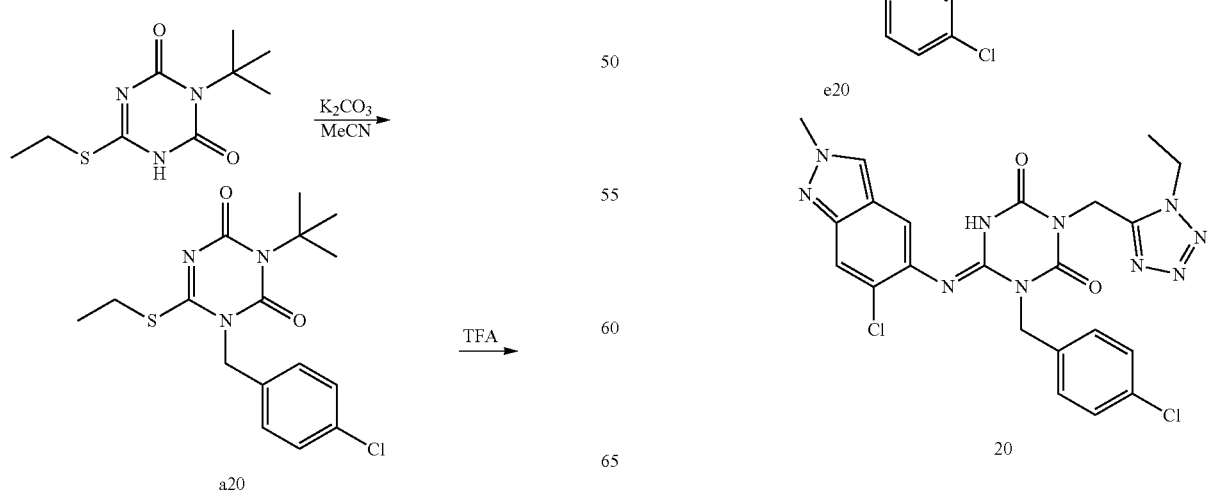

20

The preparation method was as described in Example 16, except that the corresponding raw materials were replaced. Yield of Compound 20 obtained: 37.30%.

$^1$H NMR (600 MHz, MeOD) δ 9.85 (s, 1H), 8.71 (s, 1H), 7.64 (s, 1H), 7.40-7.12 (m, 2H), 6.53 (m, 2H), 5.32-5.02 (m, 4H), 4.11 (s, 3H), 3.84 (s, 2H), 1.49 (s, 3H).

$^{13}$C NMR (151 MHz, MeOD) δ 168.21, 161.52, 152.85, 148.34, 143.14, 141.36, 137.35, 133.42, 124.84, 124.21, 117.41, 112.87, 109.14, 105.27, 104.64, 100.12, 46.02, 42.67, 40.98, 15.97.

MS calcd for $C_{22}H_{20}Cl_2N_{10}O_2$, $[M+H]^+$: 528; found: 528.

Example 21

Preparation of Compound 21: (E)-6-(6-chloro-2-methyl-2H-indazol-5-yl)imino)-3-(1-cyclopropyl-1H-tetrazol-5-yl)methyl)-1-(2,4,5-trifluorobenzyl)-1,3,5-triazin-2,4-dione (1) Preparation of Compound a21

The preparation method was the same as that in Example 1.

(2) Preparation of Compound c21

The preparation method was the same as that in Example 1.

(3) Preparation of Compound d21

The preparation method was the same as that in Example 1.

(4) Preparation of Compound 21

Sodium azide (598.1 mg, 9.2 mmol) and bromocyclopropane (240 μL, 3 mmol) were added to a reactor, dissolved in 5 mL of dry DMF, and reacted overnight with stirring at 60° C. The reaction was monitored by TLC. After the reaction was completed, the reaction solution was cooled to room temperature. The reaction mixture was extracted with brine and tetrahydrofuran. The tetrahydrofuran layer was collected, washed with a 5% lithium chloride solution and dried over MgSO4, to obtain azidocyclopropane.

Compound d1 (142.7 mg, 0.3 mmol), azidocyclopropane (29.9 mg, 0.36 mmol), copper sulfate pentahydrate (30.0 mg, 0.12 mmol), and sodium ascorbate (23.8 mg, 0.12 mmol) were added to a reactor, dissolved in a mixture of 10 mL of tetrahydrofuran and 1 mL of water, and reacted overnight by heating at 45° C. with stirring under nitrogen atmosphere. The reaction was monitored by TLC. After the reaction was completed, the obtained reaction solution was concentrated under reduced pressure to remove the solvent. The residue was separated and purified by column chromatography (mobile phase: dichloromethane:methanol (V:V)=12:1), and dried to obtain Compound 1 (35.2 mg, yield 21.03%).

$^1$H NMR (600 MHz, MeOD) δ 8.26 (s, 1H), 8.12 (s, 1H), 7.78 (s, 1H), 7.59-7.38 (m, 1H), 7.31-7.08 (m, 1H), 5.41-5.30 (m, 4H), 4.10 (s, 3H), 2.35 (s, 1H), 1.28-0.90 (m, 4H).

$^{13}$C NMR (151 MHz, MeOD) δ 178.49, 164.71, 156.16, 153.26, 149.50, 148.59, 147.92, 128.99, 127.78, 125.54, 120.34, 117.51, 116.93, 116.26, 116.01, 105.50, 104.45, 48.06, 39.57, 38.23, 28.57, 2.15.

MS calcd for $C_{23}H_{18}ClF_3N_{10}O_2$, $[M+H]^+$: 559; found: 559.

Example 22

Preparation of Compound 22: (E)-6-(6-chloro-2-methyl-2H-indazol-5-yl)imino)-3-(1-isopropyl-1H-tetrazol-5-yl)methyl)-1-(2,4,5-trifluorobenzyl)-1,3,5-triazin-2,4-dione

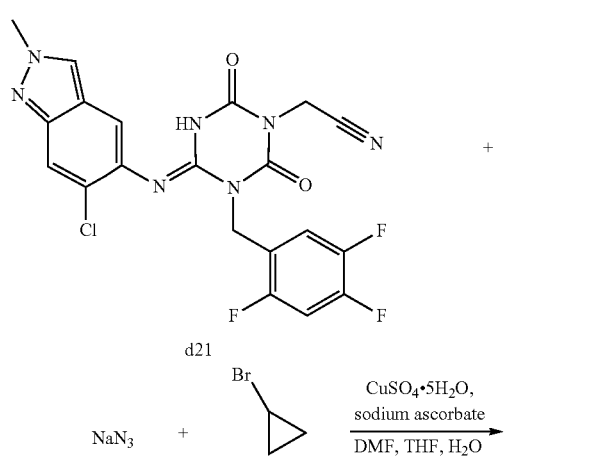

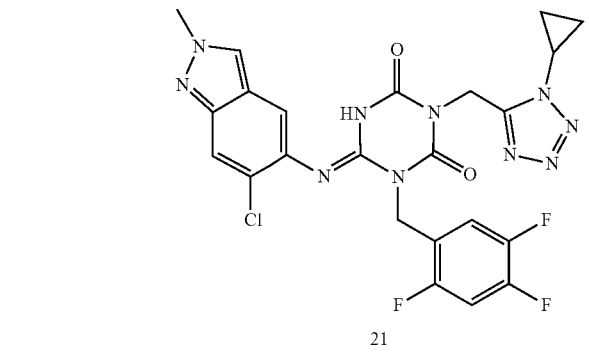

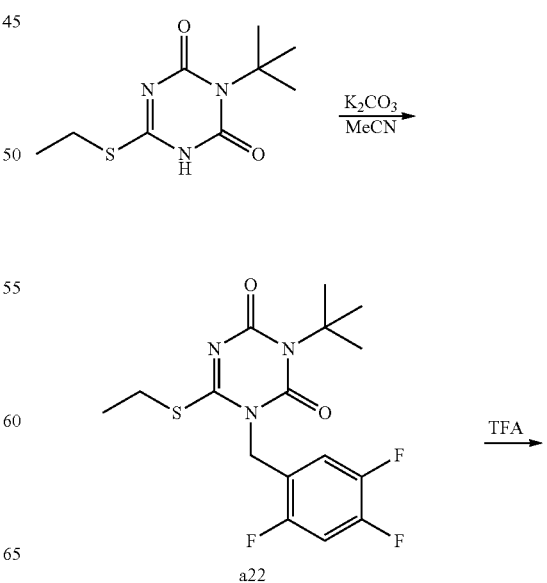

-continued

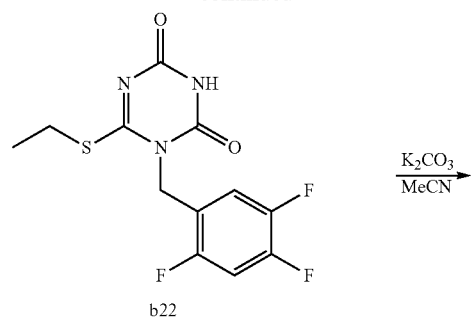
b22

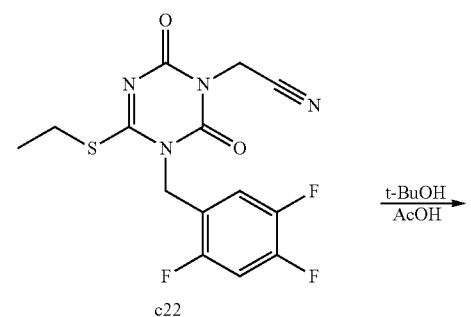
c22

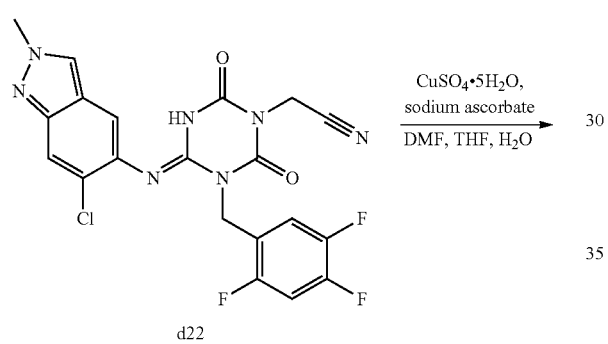
d22

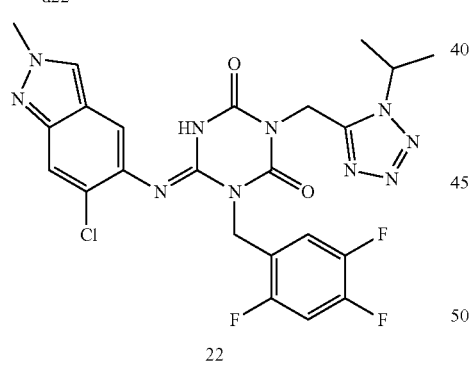
22

The preparation method was as described in Example 21, except that the corresponding raw materials were replaced. Yield of Compound 22 obtained: 32.31%.

$^1$H NMR (600 MHz, MeOD) δ 8.16 (s, 1H), 8.02 (s, 1H), 7.73 (s, 1H), 7.60-7.49 (m, 1H), 7.26-7.12 (m, 1H), 5.42-5.36 (m, 4H), 4.21 (s, 3H), 3.91 (s, 1H), 1.62 (s, 6H).

$^{13}$C NMR (151 MHz, MeOD) δ 173.62, 164.51, 157.52, 152.47, 148.97, 148.50, 148.21, 128.47, 127.24, 125.74, 120.42, 117.65, 117.28, 116.61, 116.24, 105.43, 104.82, 55.17, 48.28, 39.07, 38.47, 22.50.

MS calcd for $C_{23}H_{20}ClF_3N_{10}O_2$, [M+H]$^+$: 561; found: 561.

Example 23

Preparation of Compound 23: (E)-6-(6-chloro-2-methyl-2H-indazol-5-yl)imino)-3-(1-cyclobutyl-1H-tetrazol-5-yl)methyl)-1-(2,4,5-trifluorobenzyl)-1,3,5-triazin-2,4-dione

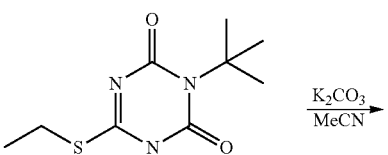

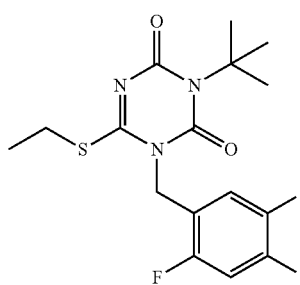
a23

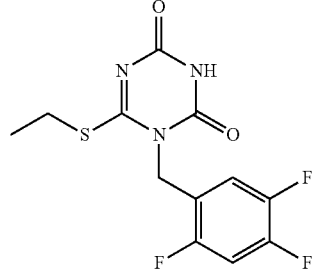
b23

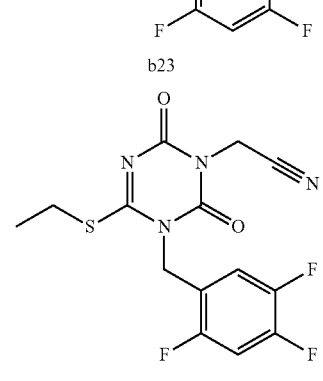
c23

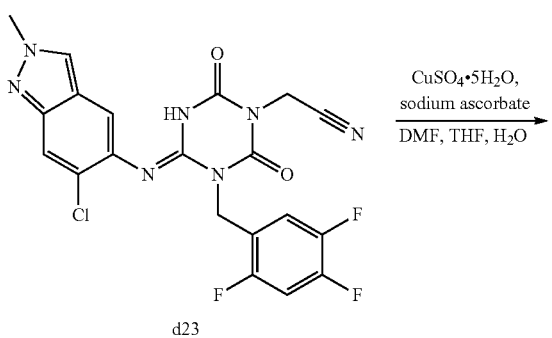
d23

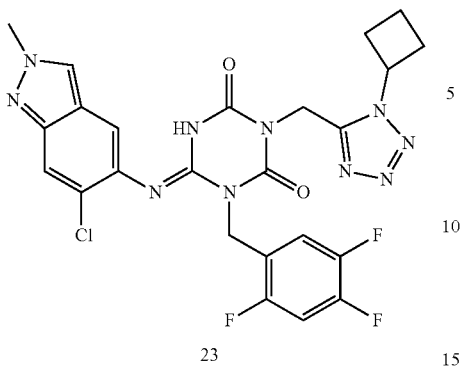

23

The preparation method was as described in Example 21, except that the corresponding raw materials were replaced. Yield of Compound 23 obtained: 37.56%.

$^1$H NMR (600 MHz, MeOD) δ 8.28 (s, 1H), 8.07 (s, 1H), 7.86 (s, 1H), 7.71-7.34 (m, 1H), 7.31-7.15 (m, 1H), 5.41-5.32 (m, 4H), 4.18 (s, 3H), 4.01 (s, 1H), 2.31-1.69 (m, 6H).

$^{13}$C NMR (151 MHz, MeOD) δ 175.62, 165.53, 156.47, 151.05, 148.87, 147.51, 147.02, 129.92, 128.31, 124.32, 120.65, 118.28, 117.61, 116.24, 115.43, 105.82, 104.17, 55.82, 48.70, 39.47, 38.05, 27.18, 14.25.

MS calcd for $C_{24}H_{20}ClF_3N_{10}O_2$, [M+H]$^+$: 573; found: 573.

Example 24

Preparation of Compound 24: (E)-6-(6-chloro-2-methyl-2H-indazol-5-yl)imino)-3-(1-isobutyl-1H-tetrazol-5-yl)methyl)-1-(2,4,5-trifluorobenzyl)-1,3,5-triazin-2,4-dione

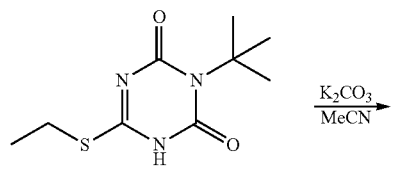

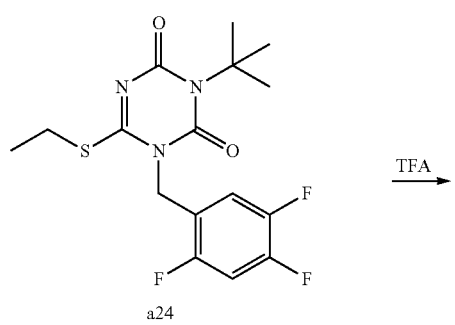
a24

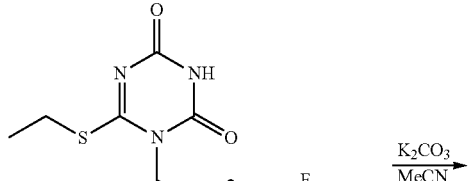
b24

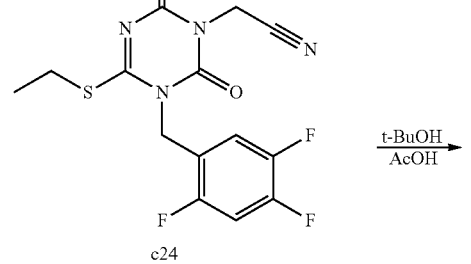
c24

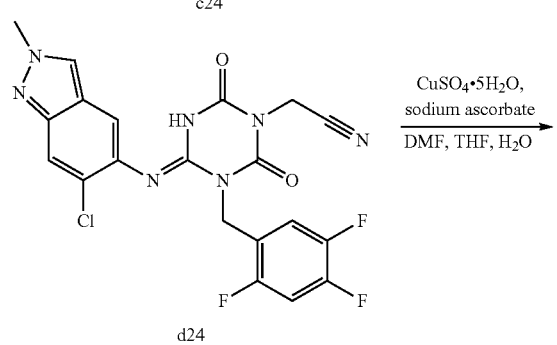
d24

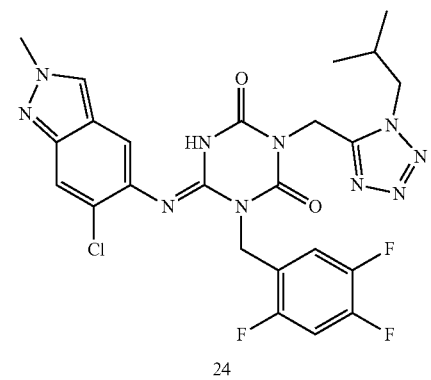
24

The preparation method was as described in Example 21, except that the corresponding raw materials were replaced. Yield of Compound 24 obtained: 39.22%.

$^1$H NMR (600 MHz, MeOD) δ 8.51 (s, 1H), 8.13 (s, 1H), 7.84 (s, 1H), 7.59-7.31 (m, 1H), 7.25-7.09 (m, 1H), 5.51-5.25 (m, 4H), 4.19 (s, 3H), 3.57 (s, 1H), 2.01 (s, 2H), 0.92 (s, 6H).

$^{13}$C NMR (151 MHz, MeOD) δ 174.63, 163.23, 156.26, 153.98, 149.06, 148.93, 148.14, 128.27, 127.56, 125.19, 120.39, 118.23, 117.94, 116.61, 115.91, 105.15, 104.90, 51.41, 48.18, 39.05, 38.24, 28.42, 18.06.

MS calcd for $C_{24}H_{22}ClF_3N_{10}O_2$, [M+H]$^+$: 575; found: 575.

2. Biological Activity Test (1) Test of Inhibitory Activity against 3CL$^{pro}$ The inhibitory activity of the compounds against SARS-CoV-2 3CL$^{pro}$ was determined by fluorescence resonance energy transfer technique.

A suitable amount of the above compounds was respectively weighed, and formulated in DMSO to give solutions over suitable concentration gradients. 5 μL of the formulated solution and 91 μL of Assay Reagent (Assay Buffer: 2019-nCoV M$^{pro}$/3CL$^{pro}$=90:1, purchased from Shanghai Beyotime Biotechnology Co., Ltd.) were added to a 96-well black plate, mixed uniformly, and incubated for 10 min at 37° C. in the dark. 4 μL of Substrate (100 μM Dabcyl-KTSAVLQSGFRKME-Edans, purchased from Shanghai Beyotime Biotechnology Co., Ltd.) was rapidly added to each well, and mixed uniformly. After incubation for 5 min at 37° C. in the dark, the signal gradually became stable. The fluorescence in 5-30 min was detected on a multifunctional plate reader (Thermo Fisher Technology Co., LTD., Varioskan Flash) and the inhibition percentage of the sample was calculated. The excitation wavelength was 340 nm and the emission wavelength was 490 nm. The Assay Reagent free of the compound was used as a control with 100% enzyme activity, the Assay Buffer free of SARS-CoV-2 M$^{pro}$/3CL$^{pro}$ was used as a blank control, and S-216722 (Shandong Xuanshuo Medical Technology Co., Ltd.) and PF-07321332 (Jinan Jianfeng Chemical Co., Ltd.) were used as positive controls. The rest of the treatment method was the same. The IC$_{50}$ values of the samples (Compounds 1-24 synthesized in the present invention were calculated by non-linear regression analysis using GraphPad Prism software.

$$\text{Inhibition rate (\%)} = \frac{RFU_{100\%enzymatic\ activity} - RFU_{sample}}{RFU_{100\%enzmatic\ acvitiy} - RFU_{blank\ control}} \times 100\%$$

The experimental results are shown in Tables 1 and 2 (in Table 1, in the IC$_{50}$ column, A: IC$_{50}$<200 nM, B: IC$_{50}$=200-500 nM, C: IC$_{50}$=500-1000 nM, D: IC$_{50}$>1000 nM). The example compounds all have inhibitory activity against 3CL$^{pro}$, where the inhibitory effects of Compounds 1, 12, 15, 16 and 17 on 3CL$^{pro}$ are high, with an IC$_{50}$ below 200 nM.

TABLE 1

Inhibitory activity of Compounds 1-24 against 3CL$^{pro}$

| Compound No. | IC$_{50}$ (nM) |
| --- | --- |
| 1 | A |
| 2 | C |
| 3 | C |
| 4 | C |
| 5 | B |
| 6 | B |
| 7 | D |
| 8 | C |
| 9 | D |
| 10 | B |
| 11 | C |
| 12 | A |
| 13 | C |
| 14 | C |
| 15 | A |
| 16 | A |
| 17 | A |
| 18 | B |
| 19 | B |
| 20 | B |
| 21 | B |
| 22 | B |
| 23 | C |
| 24 | D |

TABLE 2

Inhibitory activity of Compounds 1, 12, 17, S-217622 and PF-07321332 against 3CL$^{pro}$

| | Compounds | | | | |
| --- | --- | --- | --- | --- | --- |
| Concentration/nM | S-217622 (IC$_{50}$ = 33.02 nM) | PF-07321332 (IC$_{50}$ = 46.98 nM) | 1 (IC$_{50}$ = 119.7 nM) | 12 (IC$_{50}$ = 183.7 nM) | 17 (IC$_{50}$ = 160.0 nM) |
| 1000 | 94.01% | 89.68% | 89.12% | 85.42% | 85.36% |
| 500 | 90.80% | 73.84% | 73.44% | 70.23% | 68.52% |
| 100 | 77.55% | 60.74% | 58.21% | 40.01% | 44.76% |
| 50 | 55.62% | 56.31% | 21.89% | 18.76% | 25.23% |
| 30 | 47.83% | 43.96% | 18.23% | 12.31% | 17.92% |
| 20 | 39.52% | 41.05% | 14.30% | 9.30% | 12.76% |
| 10 | 25.77% | 26.18% | 9.75% | 7.28% | 7.67% |
| 5 | 14.64% | 12.91% | 7.77% | 4.98% | 6.21% |
| 1 | 5.02% | 4.79% | 2.12% | 1.86% | 1.93% |
| 0.1 | 0.84% | 0.59% | 0.86% | 0.52% | 0.76% |

Figure 4:
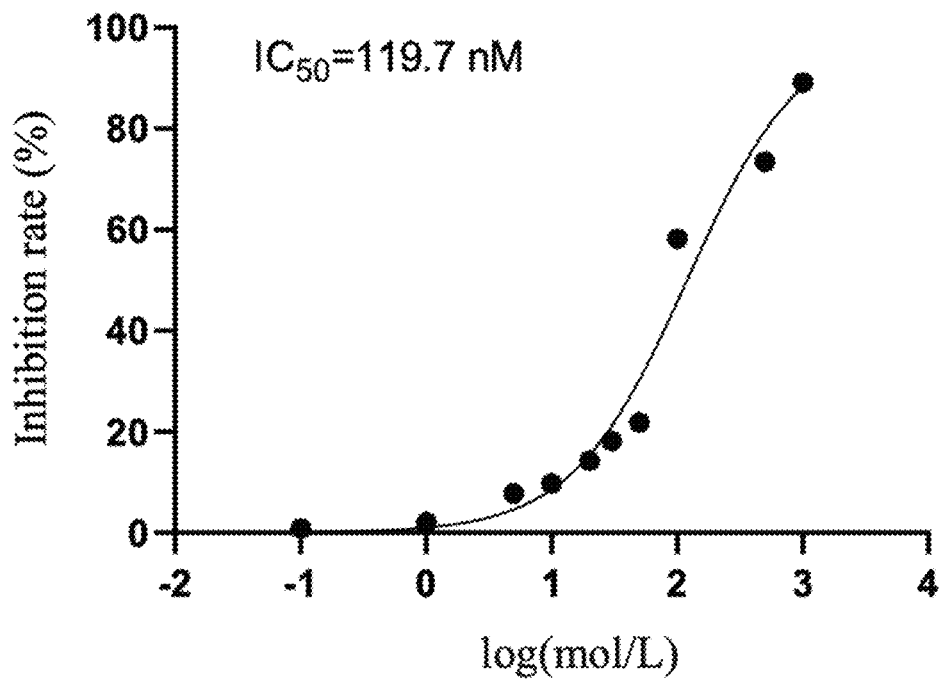
FIG. 4 shows the inhibition of Compound 1 of the present invention on 3CL$^{pro}$.
Figure 5:
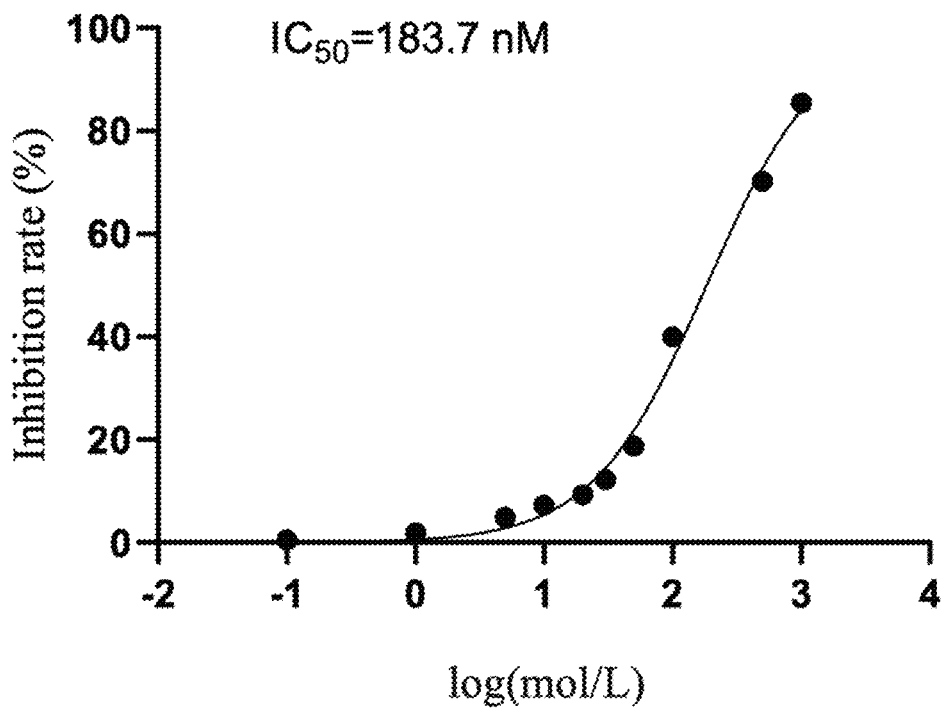
FIG. 5 shows the inhibition of Compound 12 of the present invention on 3CL$^{pro}$.
Figure 6:
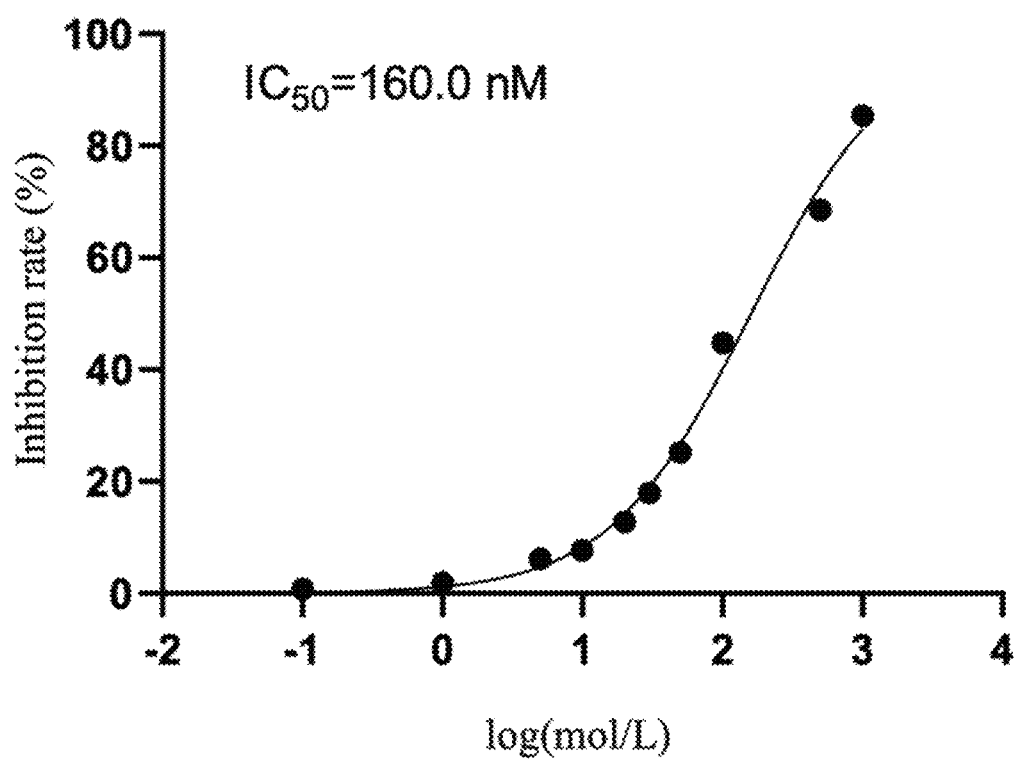
FIG. 6 shows the inhibition of Compound 17 of the present invention on 3CL$^{pro}$.

The data in Tables 1-2 shows that Compounds 1-24 have different inhibitory effects on 3CL$^{pro}$. The IC$_{50}$ values of Compounds 1, 12, 15, 16 and 17 for 3CL$^{pro}$ are all below 200 nM, suggesting that the 3-tetrazolylmethyl-1,3,5-triazin-2,4-dione compound according to the present invention has inhibitory activity against coronavirus 3CL$^{pro}$. FIGS. 4-6 respectively show the inhibitory effects of Compounds 1, 12 and 17 having the most desirable inhibitory activity on 3CL$^{pro}$, where Compound 1 has a better inhibitory effect than Compounds 12 and 17, and can be used as developed and used as anti-coronavirus drugs.

(2) Cytotoxicity Test

Figure 7:
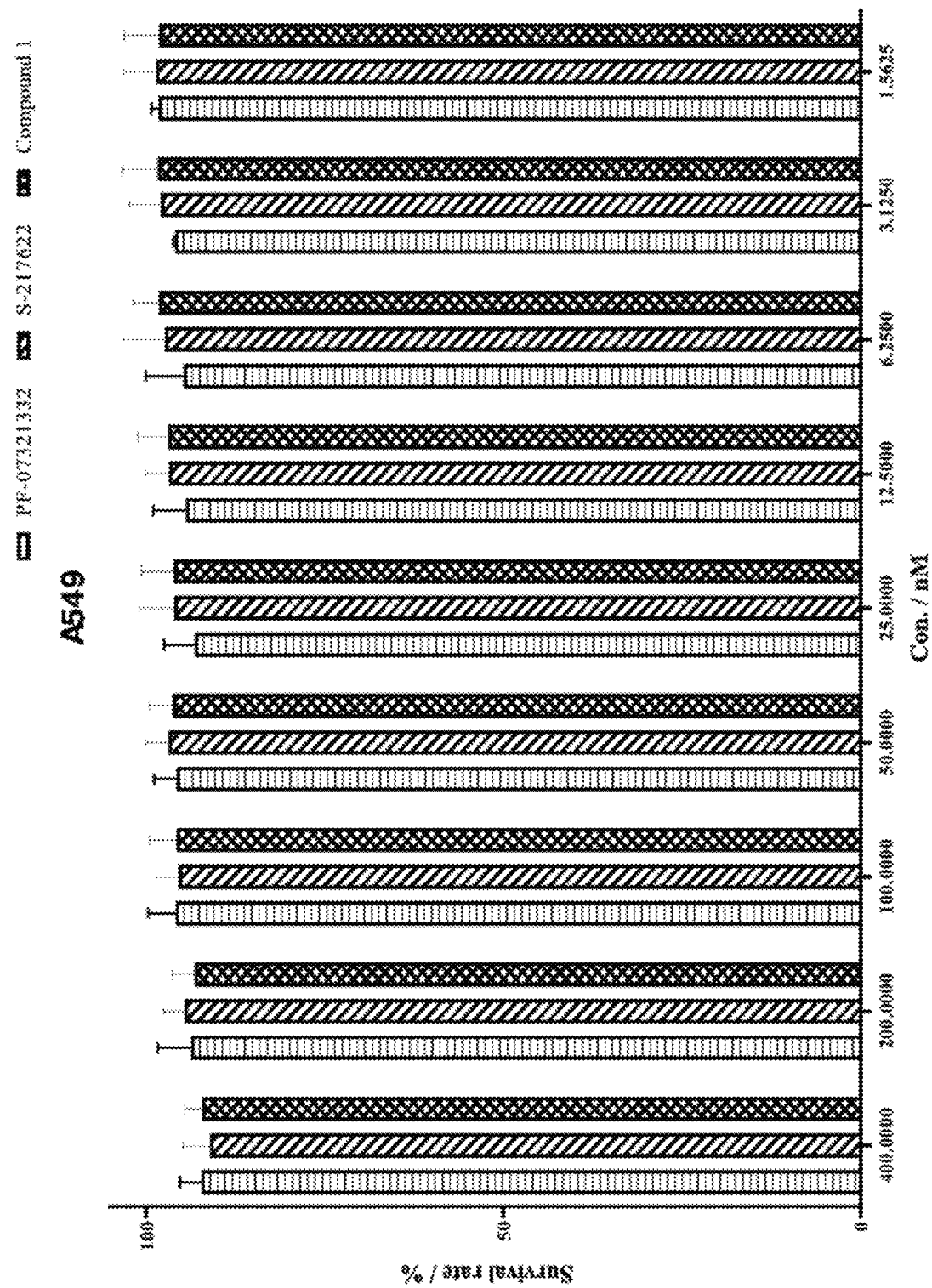
FIG. 7 shows the survival rate of A549 cells in the presence of various concentrations of PF-07321332, S-217622, and Compound 1.
Figure 8:
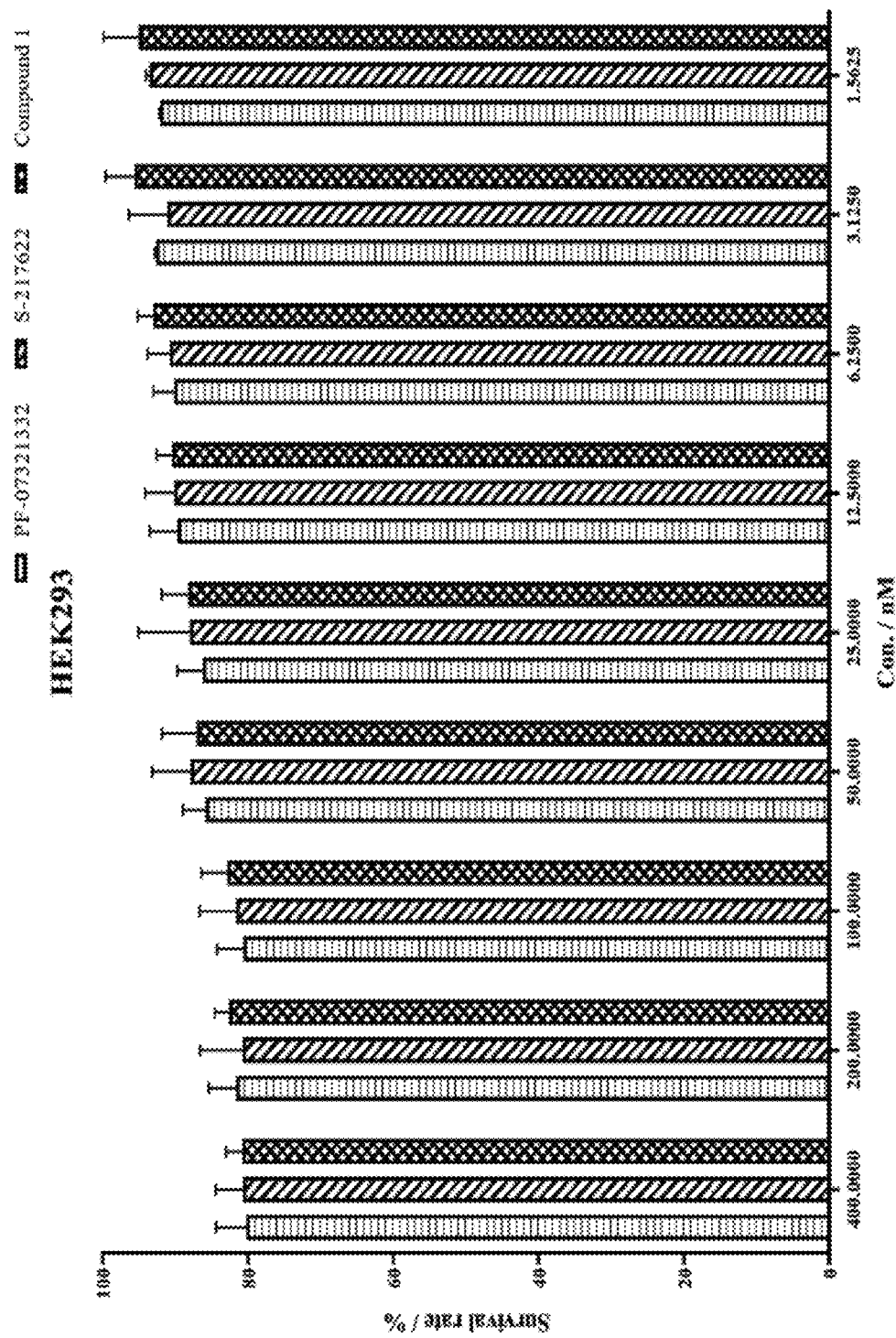
FIG. 8 shows the survival rate of HEK2932 cells in the presence of various concentrations of PF-07321332, S-217622, and Compound 1.
Figure 9:
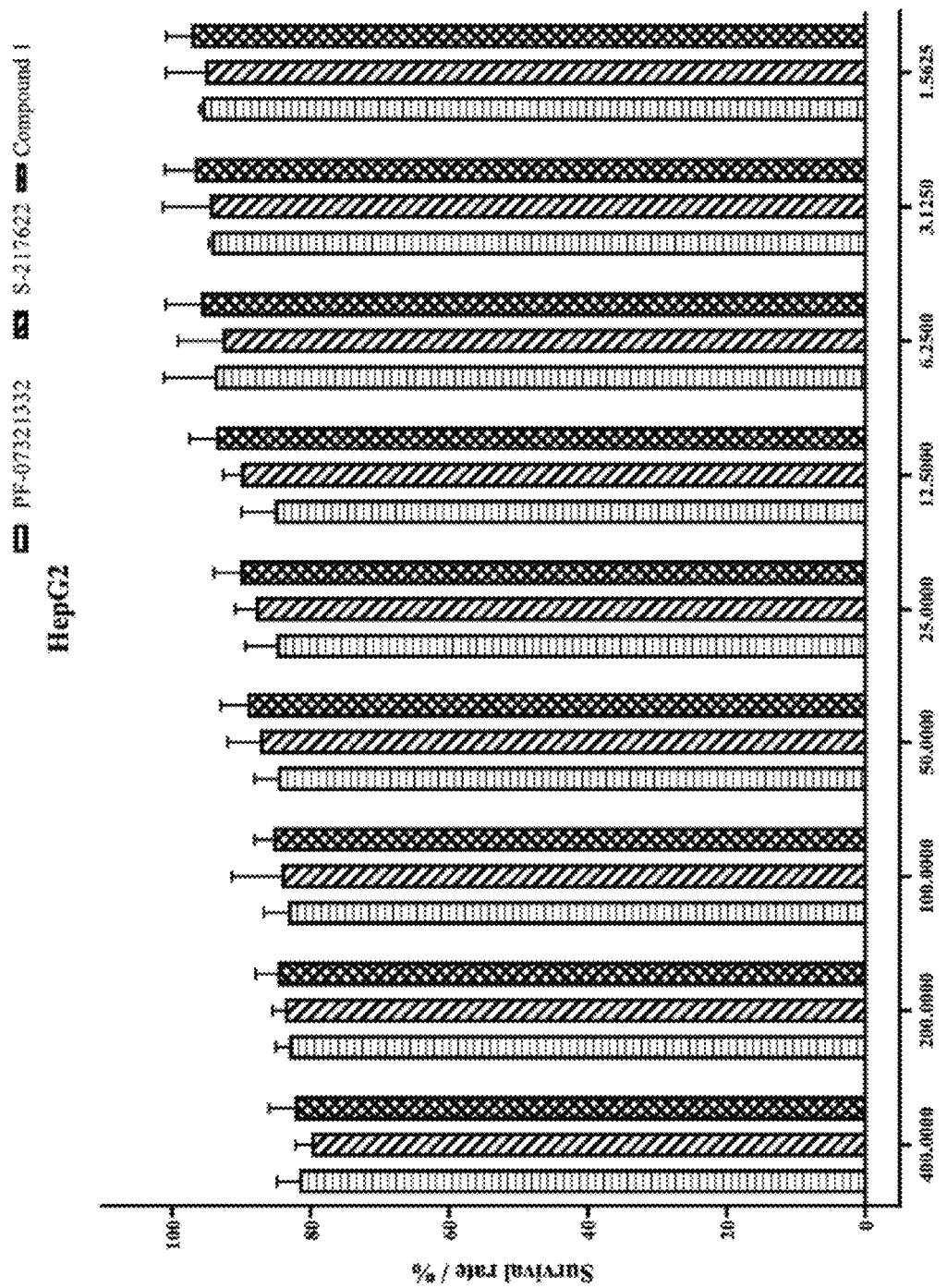
FIG. 9 shows the survival rate of HepG2 cells in the presence of various concentrations of PF-07321332, S-217622, and Compound 1.

The in-vitro cytotoxicity of Compounds 1, 12, and 17 was evaluated by the MTT method. HepG2, HEK293 and A549 cells in logarithmic growth phase were respectively trypsinized into a cell suspension. The cell density was adjusted to 5×10$^4$ cells/mL. 180 µL per well of the cell suspension was inoculated into a sterile 96-well plate at 37° C., and cultured in an incubator at 5% CO$_2$ for 24 hrs. After the cells were attached to the bottom of the plate, 20 µL of the drug solutions over the concentration gradients were respectively added into each well, and 6 replicate wells were set in parallel. Also, a blank group (group without cells and drug) and a control group (group without drug) were set. The system was incubated in an incubator at 37° C. and 5% CO$_2$ for 24 hrs, and then 20 µL per well of a 5 g/L MTT solution was added and incubated for another 4 hrs. After the incubation was completed, the culture medium in the well was gently aspirated, and 100 µL of DMSO was added to each well. Then the crystal was fully dissolved in a shaker for 10 min at a low speed. After that, the absorbency of each well was measured at OD$_{490\ nm}$ in an enzymelinked immunodetector, and the survival rate of cells was calculated. The results are shown in Tables 3-5, and FIGS. 7-9.

$$\text{Cell survival rate} = \frac{OD\ \text{treatment group} - OD\ \text{blank group}}{OD\ \text{control group} - OD\ \text{blank group}}$$

TABLE 3

Effects of test drugs on A549 cells
Survival rate of A549 cells

| Concentration (nM) | 400 | 200 | 100 | 50 | 25 | 12.5 | 6.25 | 3.125 | 1.5625 |
|---|---|---|---|---|---|---|---|---|---|
| PF-07321332 | 92.31% | 93.74% | 95.91% | 95.76% | 93.21% | 94.43% | 94.77% | 96.01% | 98.28% |
| S-217622 | 91.09% | 94.62% | 95.46% | 96.92% | 96.09% | 96.81% | 97.39% | 97.96% | 98.63% |
| 1 | 92.19% | 93.23% | 95.75% | 96.33% | 96.16% | 96.93% | 98.23% | 98.39% | 98.18% |
| 12 | 89.12% | 92.13% | 93.51% | 93.96% | 95.19% | 96.42% | 96.86% | 96.76% | 98.43% |
| 17 | 91.33% | 93.31% | 94.21% | 94.13% | 95.77% | 96.38% | 97.24% | 97.96% | 98.02% |

TABLE 4

Effects of test drugs on HEK293 cells
Survival rate of HEK293 cells

| Concentration (nM) | 400 | 200 | 100 | 50 | 25 | 12.5 | 6.25 | 3.125 | 1.5625 |
|---|---|---|---|---|---|---|---|---|---|
| PF-07321332 | 80.26% | 81.64% | 80.62% | 85.81% | 86.22% | 89.70% | 90.14% | 92.68% | 92.10% |
| S-217622 | 80.71% | 80.75% | 81.65% | 87.90% | 87.99% | 90.14% | 90.77% | 91.12% | 93.54% |
| 1 | 80.83% | 82.56% | 82.87% | 87.10% | 88.23% | 90.50% | 93.10% | 95.62% | 95.07% |
| 12 | 77.46% | 78.93% | 82.76% | 82.99% | 85.34% | 89.80% | 91.16% | 92.73% | 93.44% |
| 17 | 78.03% | 79.45% | 83.83% | 84.32% | 85.73% | 90.79% | 93.48% | 93.12% | 93.79% |

TABLE 5

Effects of test drugs on HepG2 cells
Survival rate of HepG2 cells

| Concentration (nM) | 400 | 200 | 100 | 50 | 25 | 12.5 | 6.25 | 3.125 | 1.5625 |
|---|---|---|---|---|---|---|---|---|---|
| PF-07321332 | 81.61% | 83.06% | 83.22% | 84.71% | 84.94% | 85.17% | 93.86% | 94.29% | 95.60% |
| S-217622 | 79.89% | 83.68% | 84.16% | 87.29% | 87.94% | 90.01% | 92.69% | 94.49% | 95.19% |
| 1 | 82.33% | 84.76% | 85.37% | 89.09% | 90.15% | 93.62% | 95.83% | 96.73% | 97.17% |
| 12 | 77.32% | 82.56% | 83.43% | 87.52% | 88.16% | 91.45% | 93.92% | 94.78% | 96.16% |
| 17 | 76.13% | 80.42% | 83.85% | 87.13% | 90.46% | 91.02% | 94.43% | 95.79% | 95.56% |

Tables 3-5 show the inhibition rates of PF-PF-07321332, S-217622, representative Compounds 1, 12 and 17 on A549, HEK293 and HepG2 cells at various concentrations. From the above data and FIGS. 7-9, it can be known that the inhibition rates of Compound 1 on HepG2 and HEK293 cells are lower than those of PF-07321332 and S-217622 at any concentrations, and the toxicity to A549 cells is better than that of PF-07321332 and S-217622 at low concentrations. The toxicity of Compound 12 and Compound 17 to the three test cells was slightly higher than that of PF-07321332 and S-217622 at 400 nM and 200 nM; however, when Compound 12 and Compound 17 are used in the treatment of HEK293 and HepG2 cells at a concentration of 12.5 nM or lower, the cells survival rates are higher than those obtained with PF-07321332 and S-217622, but less than that obtained with Compound 1. Based on the above data, the test Compound 1 has good inhibitory activity against 3CL protease and low toxicity, and can be further studied.

The above disclosure is provided merely for explaining the technical idea of the present invention, and cannot be regarded as limiting the protection scope of the present invention. Any changes made on the basis of the technical solution according to the technical idea proposed by the present invention fall within the protection scope as defined by the claims of the present invention.

The invention claimed is:

1. A compound of formula I, a pharmaceutically acceptable salt thereof, or a tautomer thereof,

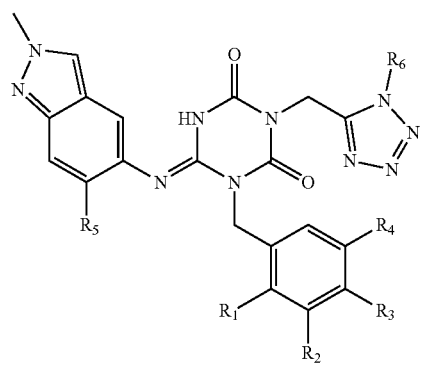

I wherein $R_1$, $R_2$, $R_3$, and $R_4$ are each independently selected from the group consisting of hydrogen, methyl, t-butyl, methoxy, difluoromethyl, trifluoromethyl, trifluoromethoxy, nitro, halo, phenyl and heteroarylcyclyl; $R_5$ is hydrogen or halo; $R_6$ is hydrogen, or an alkyl or cycloalkyl having 1 to 4 carbon atoms; and wherein the compound inhibits coronavirus 3CL protease activity.

2. The compound according to claim 1, wherein the compound is selected from the group consisting of:

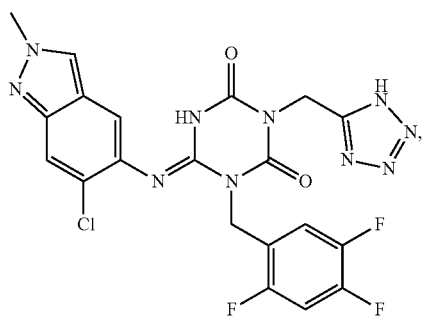

1

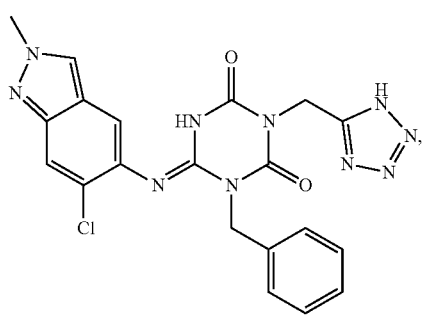

2

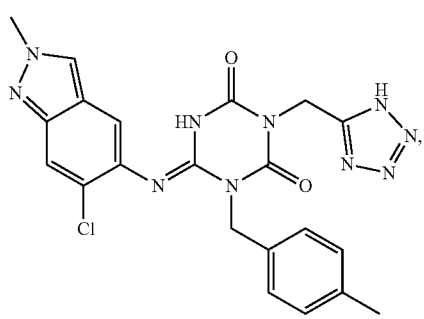

3

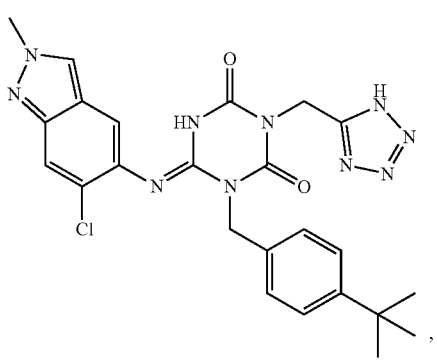

4

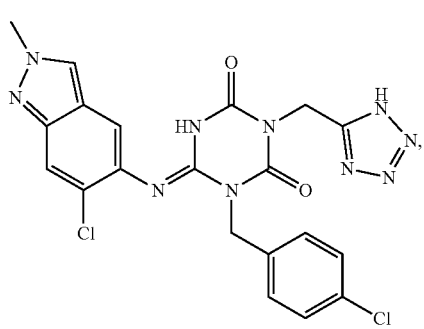

5

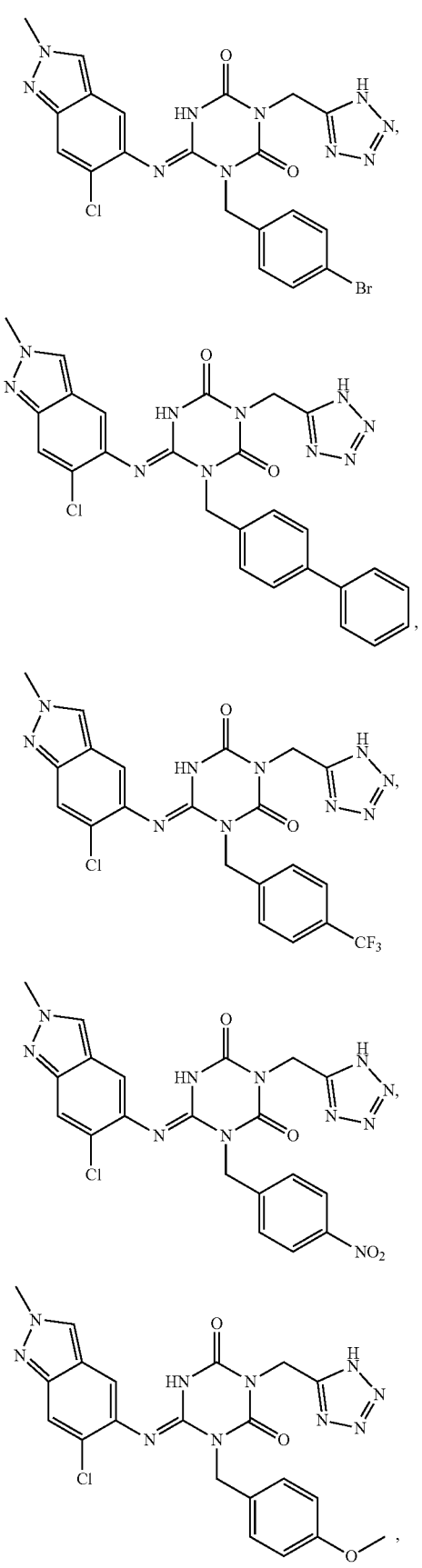
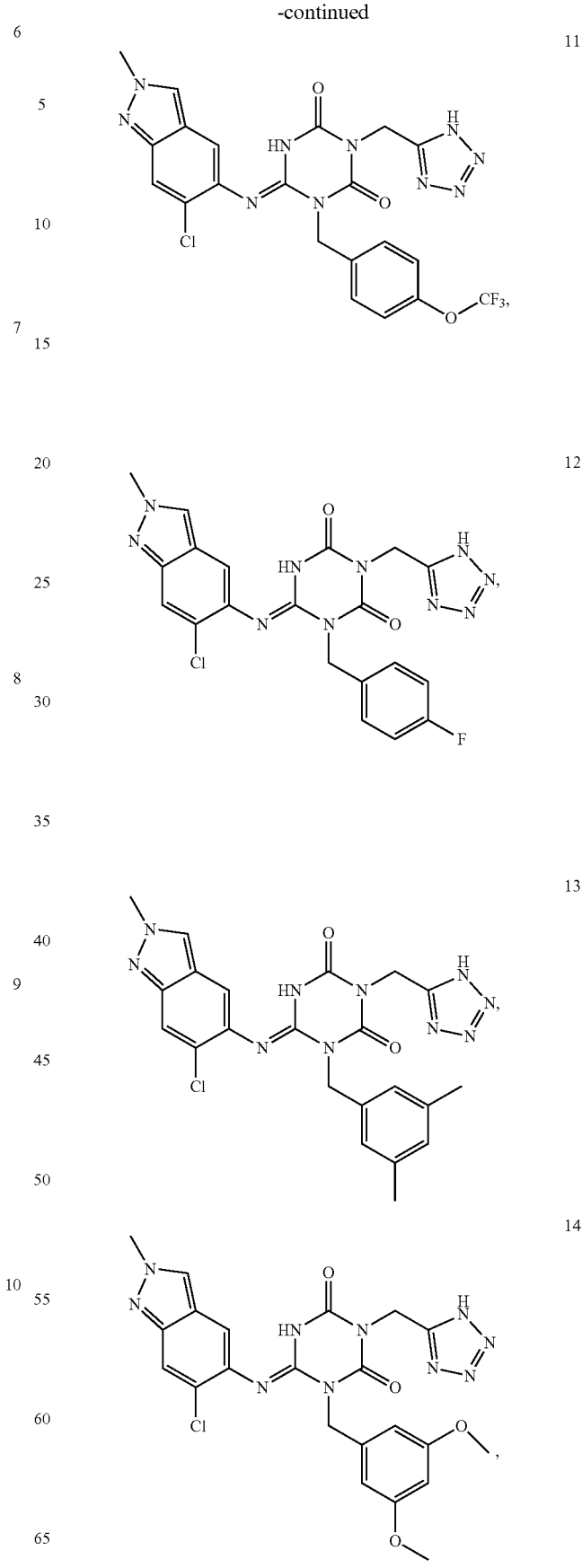

15
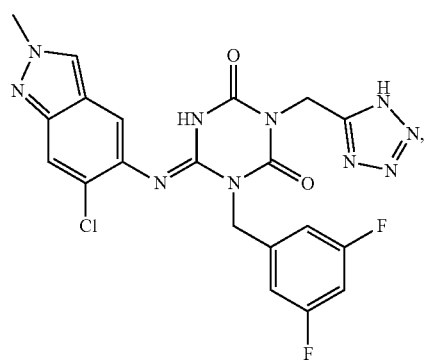
16
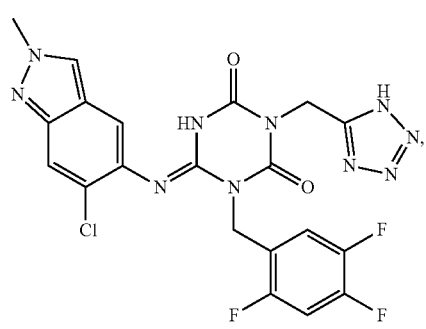
17
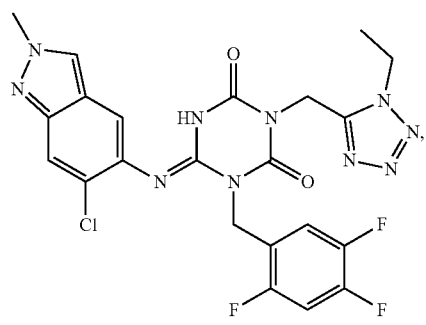
18
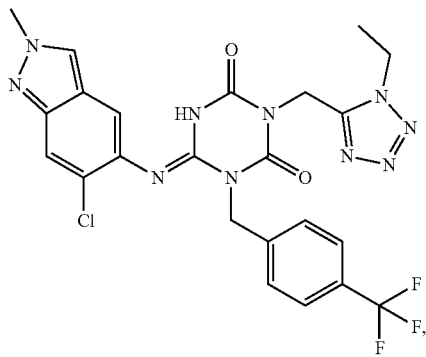
19
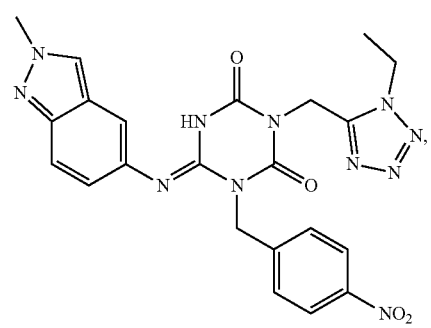
20
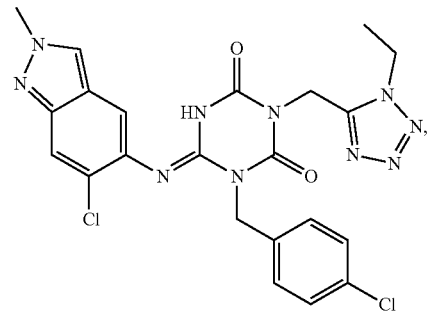
21
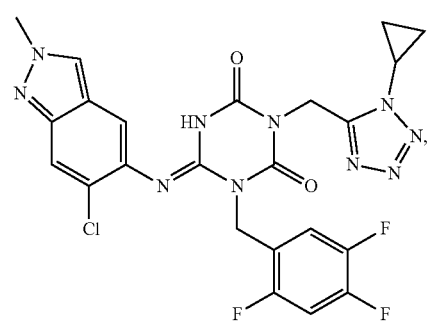
22
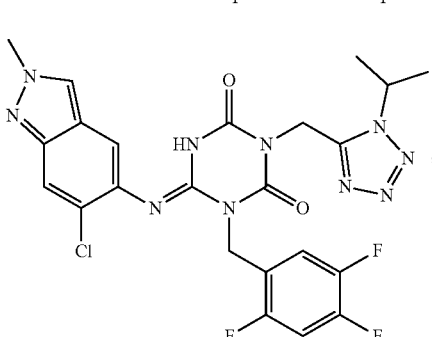,
23
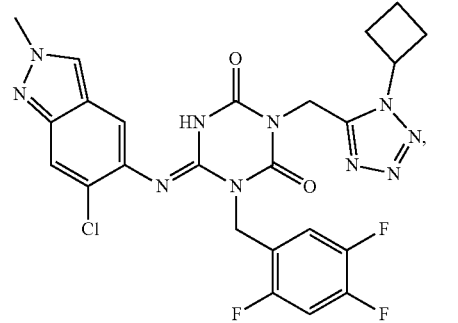 and -continued

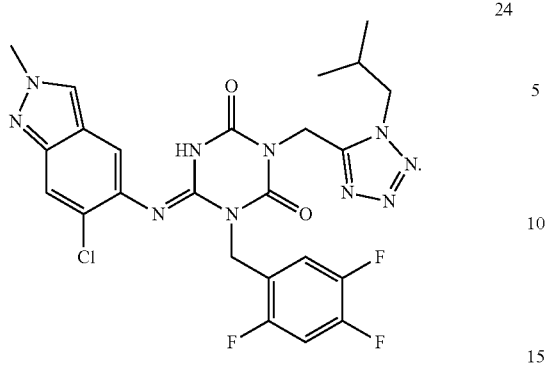

24

3. The compound according to claim 1, wherein a salt of the pharmaceutically acceptable salt is hydrochloric acid, hydrobromic acid, sulfuric acid, nitric acid, phosphoric acid, acetic acid, fumaric acid, maleic acid, oxalic acid, malonic acid, succinic acid, citric acid, malic acid, methansulfonic acid, ethansulfonic acid, benzenesulfonic acid, toluenesulfonic acid, glutamic acid, or aspartic acid.

4. A pharmaceutical composition, comprising the compound according to claim 1 as an active ingredient.

* * * * *